United States Patent
Koentgen et al.

(10) Patent No.: US 6,590,080 B1
(45) Date of Patent: Jul. 8, 2003

(54) CATALYTIC ANTIBODIES AND A METHOD OF PRODUCING SAME

(75) Inventors: Frank Koentgen, 5 Timberglades, Park Orchards, Victoria 3114 (AU); Gabriele Maria Suess, Park Orchards (AU); David Mathew Tarlinton, Blackburn (AU); Herbert Rudolf Treutlein, Moonee Ponds (AU)

(73) Assignee: Frank Koentgen, North Beach (AU)

( * ) Notice: Subject to any disclaimer, the term of this patent is extended or adjusted under 35 U.S.C. 154(b) by 0 days.

(21) Appl. No.: 09/509,031

(22) PCT Filed: Sep. 18, 1998

(86) PCT No.: PCT/AU98/00783

§ 371 (c)(1),
(2), (4) Date: Jun. 9, 2000

(87) PCT Pub. No.: WO99/15563

PCT Pub. Date: Apr. 1, 1999

(30) Foreign Application Priority Data

Sep. 19, 1997 (AU) .............................. PO9306

(51) Int. Cl.[7] .......................... C07K 14/60; C12N 9/00
(52) U.S. Cl. ..................................... 530/399; 435/188.5
(58) Field of Search ...................... 435/188.5; 530/350, 530/399

(56) References Cited

U.S. PATENT DOCUMENTS

| | | | | |
|---|---|---|---|---|
| 4,888,281 A | * | 12/1989 | Schochetman et al. | 435/72 |
| 4,900,674 A | * | 2/1990 | Benkovic et al. | 435/232 |
| 5,126,258 A | * | 6/1992 | Lerner et al. | 435/188.5 |
| 5,187,086 A | * | 2/1993 | Janda et al. | 435/146 |
| 5,190,865 A | * | 3/1993 | Schultz | 435/108 |
| 5,219,732 A | * | 6/1993 | Schultz | 435/41 |
| 5,302,516 A | * | 4/1994 | Schultz | 435/41 |
| 5,439,812 A | * | 8/1995 | Benkovic et al. | 435/109 |

OTHER PUBLICATIONS

Janda, K.D., et al. (1991) Tetrahedron 47 (14/15), 2503–2506.*

* cited by examiner

*Primary Examiner*—Charles L. Patterson, Jr.
(74) *Attorney, Agent, or Firm*—Scully, Scott, Murphy & Presser

(57) ABSTRACT

The present invention relates generally to a growth factor precursor and its use to select production of antigen specific catalytic antibodies. Such catalytic antibodies are produced following B cell activation and proliferation induced by catalytic cleavage products of a target antigen portion of the growth factor precursor of the present invention. A particularly useful form of the growth factor precursor is as a nucleic acid vaccine. The nucleic acid vaccine of the present invention preferably further LgL

B7-1

B7-2

Fluorescence Intensity

CATALYTIC ANTIBODIES AND A METHOD OF PRODUCING SAME

FIELD OF THE INVENTION

The present invention relates generally to a growth factor precursor and its use to select production of antigen specific catalytic antibodies. Such catalytic antibodies are produced following B cell activation and proliferation induced by catalytic cleavage products of a target antigen portion of the growth factor precursor of the present invention. A particularly useful form of the growth factor precursor is as a nucleic acid vaccine. The nucleic acid vaccine of the present invention preferably further comprises a molecular adjuvant. Another aspect of the present invention comprises a growth factor precursor in multimeric form. The growth factor precursor of the present invention is useful for generating catalytic antibodies for both therapeutic, diagnostic and industrial purposes.

BACKGROUND OF THE INVENTION

The rapidly increasing sophistication of recombinant DNA technology is greatly facilitating research and development in the medical and allied health fields. A particularly important area of research is the use of recombinant antigens to stimulate immune response mechanisms and outcomes. However, recombinant techniques have not been fully effective in generating all components of the humoral response. One such important yet not fully exploited component is the catalytic antibody.

Catalytic antibodies are highly substrate specific catalysts which can be used, for example, to proteolytically activate or inactivate proteins. Catalytic antibodies have great potential as therapeutic agents in human diseases such as rheumatoid arthritis, AIDS and Alzheimer's disease amongst many others.

Antibody therapy has been used in patients. Antibodies have a half-life of about 23 days in the circulation of humans which is a clear advantage over other drugs. Catalytic antibodies, however, are considered to be even more effective. They are recycled after their antigenic encounter and are not bound to the antigen as occurs with "classical" antibodies. Catalytic antibodies should, therefore, function at a much lower dose than classical antibodies and could be used at sub-immunogenic doses. Catalytic antibodies would be particularly useful in long term therapy.

Traditionally, catalytic antibodies have been generated by immunising mice with transition state analogs. Such antibodies have been shown to catalyse several chemical reactions. However, this approach has a severe limitation in that it is difficult to predict the structure of transition state analogs which effect proteolysis of specific proteins. Immunising a mouse with a transition state analog is by definition inefficient since it selects B cells on the ability of surface immunoglobulins to bind the analogs and not on the ability of a surface immunoglobulins to catalytically cleave the analogue. This is one of the reasons why catalytic antibodies have relatively low turn-over rates and cannot compete with the naturally occurring enzyme counterparts, in the case where they exist.

Another approach has been the mutation of conventional antibodies to alter their activity to be catalytical like in nature. However, to date, such an approach has not proved successful.

As a consequence, catalytic antibodies have not previously achieved prominence as therapeutic, diagnostic or industrial tools.

There is a need, therefore, to develop a more efficacious approach to generating catalytic antibodies having desired catalytic specificity.

International Patent Application No. PCT/AU97/00194 filed on Mar. 26, 1997 and is herein incorporated by reference provided a means for selecting catalytic B cells. The method contemplated a growth factor comprising two Ig binding domains from protein L of *Peptostreptococcus magnus* as B cell surface molecule binding portions flanking a T cell surface molecule binding portion (designated "H") from hen egg lysozyme (HEL). The specificity of the LHL growth factor for catalytic B cells was provided by an antigen masking or attached to a molecule masking one or more of the B cell surface molecule binding portions. Catalytic cleavage of the antigen exposed the B cell surface molecule binding portions to permit catalytic antibody production.

In accordance with the present invention, there is provided an improved growth factor precursor.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Sequence Identity Numbers (SEQ ID NOs.) for nucleotide and amino acid sequences referred to herein are defined following the Examples.

One aspect of the present invention is directed to a growth factor precursor comprising a recombinant polypeptide chain or a molecule having modular peptide components or a synthetic equivalent thereof wherein said polypeptide chain or modular peptide molecule comprises at least one B cell surface molecule binding portion, at least one T cell surface molecule binding portion capable of providing T cell dependent help to a B cell, an antigen cleavable by a catalytic antibody and a peptide portion comprising domains from both a variable heavy chain and a variable light chain of an immunoglobulin and wherein said variable heavy chain and variable light chain domains in the growth factor precursor, associate together by intra- and/or inter-domain bonding and substantially prevent the at least one B cell surface molecule binding portion from interacting with a B cell surface molecule such that upon cleavage of said antigen by a catalytic antibody, the peptide comprising said variable heavy chain and variable light chain domain permits the at least one B cell surface molecule binding portion to interact with a B cell surface molecule.

Another aspect of the present provides a growth factor precursor comprising a recombinant polypeptide chain or a molecule having modular peptide components or a synthetic equivalent thereof wherein said polypeptide chain or modular peptide molecule comprises at least one B cell surface molecule binding portion, at least one T cell surface molecule binding portion capable of providing T cell dependent help to a B cell, an antigen cleavable by a catalytic antibody and a peptide portion comprising domains from both a variable heavy chain and a variable light chain of an immunoglobulin and wherein said variable heavy chain and variable light chain domains in the growth factor precursor associate together by intra- and/or inter-domain bonding and substantially prevent the at least one B cell surface molecule binding portion from interacting with a B cell surface molecule such that upon cleavage of said antigen by a catalytic antibody, the peptide comprising said variable heavy chain and variable light chain domain permits the at least one B cell surface molecule binding portion to interact with a B cell surface molecule wherein if said growth factor precursor comprises a single B cell surface molecule binding portion, then the growth factor precursor further comprises a multimerising inducing element.

Yet another aspect of the present invention provides a growth factor precursor comprising a recombinant polypeptide chain or a molecule having modular peptide components or a synthetic equivalent thereof wherein said polypeptide chain or modular peptide molecule comprises at least two B cell surface molecule binding portions, at least one T cell surface molecule binding portion capable of providing T cell dependent help to a B cell, an antigen cleavable by a catalytic antibody and a peptide portion comprising domains from both a variable heavy chain and a variable light chain such that in the growth factor precursor, these variable chain domains associate together by intra- and/or inter-domain bonding and, when associated together, substantially prevent at least one of the B cell surface molecule binding portions from interacting with a B cell surface molecule wherein upon cleavage of said antigen by a catalytic antibody, the at least two B cell surface molecule binding portions induce activation and proliferation of a B cell expressing said catalytic antibody.

Figure 1:
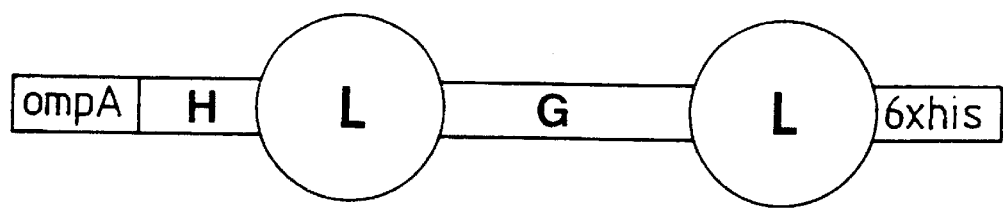
FIG. 1 is a diagrammatic representation showing the structure of LgL comprising ompA and the hexa-his-Tag on the C terminus.

The following abbreviations are used in the specification.

| | |
|---|---|
| ccMTLgL | Growth factor precursor comprising LgL linked to variable heavy and light chain domains from antibody McPc603 via TEV sensitive peptide |
| FSC | Forward light scatter |
| g | Glycine-serine linker having the structure (GGGGS)$_4$ |
| H | T cell surface molecule binding portion from hen egg lysosyme (HEL) |
| huIgG | Human immunoglobulin G |
| L | B cell surface molecule binding portion from protein L of *Peptostreptococcus magnus* |
| LgL | Two L molecules linked via glycine-serine peptide |
| LHL | Growth factor comprising H flanked by two L molecules |
| McPc603 | Antibody having anti-phosphorylcholine specificity |
| TLHL | LHL linked to kappa light chain via TEV sensitive peptide and g attached to N terminus region |

SUMMARY OF SEQ ID NOs.

| | SEQ ID NO. | |
|---|---|---|
| MOLECULE | Nucleotide | Amino acid |
| LHL | 1 | 2 |
| CATAB-TEV | 3 | 4 |
| TLHL | 5 | 6 |
| LHL.seq | 7 | 8 |
| FLAG epitope | — | 9 |
| Kappa | 10 | 11 |
| LHL-omp | 12 | 13 |
| Strep-tag | — | 14 |
| ccMTLgL | 15 | 16 |

DETAILED DESCRIPTION OF THE INVENTION

The present invention provides in part an improved growth factor precursor capable of selecting catalytic B cells. The selected catalytic B cells then undergo mitogenesis including activation and proliferation as a pre-requisite for the production of catalytic antibodies.

Accordingly, one aspect of the present invention is directed to a growth factor precursor comprising a recombinant polypeptide chain or a molecule having modular peptide components or a synthetic equivalent thereof wherein said polypeptide chain or modular peptide molecule comprises at least one B cell surface molecule binding portion, at least one T cell surface molecule binding portion capable of providing T cell dependent help to a B cell, an antigen cleavable by a catalytic antibody and a peptide portion comprising domains from both a variable heavy chain and a variable light chain of an immunoglobulin and wherein said variable heavy chain and variable light chain domains in the growth factor precursor associate together by intra- and/or inter-domain bonding and, when associated together, substantially prevent the at least one B cell surface molecule binding portion from interacting with a B cell surface molecule such that upon cleavage of said antigen by a catalytic antibody, the peptide comprising said variable heavy chain and variable light chain domain permits the at least one B cell surface molecule binding portion to interact with a B cell surface molecule wherein if said growth factor precursor comprises a single B cell surface molecule binding portion, then the growth factor precursor further comprises a multimerising inducing element.

The present invention further provides a growth factor precursor comprising a recombinant polypeptide chain or a molecule having modular peptide components or a synthetic equivalent thereof wherein said polypeptide chain or modular peptide molecule comprises at least one B cell surface molecule binding portion, at least one T cell surface molecule binding portion capable of providing T cell dependent help to a B cell, an antigen cleavable by a catalytic antibody and a peptide portion comprising domains from both a variable heavy chain and a variable light chain of an immunoglobulin and wherein said variable heavy chain and variable light chain domains in the growth factor precursor associate together by intra- and/or inter-domain bonding and, when associated together, substantially prevent the at least one B cell surface molecule binding portion from interacting with a B cell surface molecule such that upon cleavage of said antigen by a catalytic antibody, the peptide comprising said variable heavy chain and variable light chain domain permits the at least one B cell surface molecule binding portion to interact with a B cell surface molecule wherein if said growth factor precursor comprises a single B cell surface molecule binding portion, then the growth factor precursor further comprises a multimerising inducing element.

The growth factor precursor is deemed a "precursor" since it is substantially incapable of inducing B cell mitogenesis (i.e. activation and proliferation followed by antibody production) in the absence of catalytic cleavage of a portion of the growth factor precursor which masks at least one B cell surface molecule binding portion on the molecule. By masking the B cell surface molecule binding portion, the growth factor precursor is substantially incapable of inducing B cell mitogenesis such as by, but not limited to, cross-linking of B cell surface immunoglobulins. The term "masks" or "masking" includes the steric, conformational, electrostatic and/or physical interference at or proximal to at least one B cell surface molecule binding portion on the growth factor precursor thus preventing interaction between the B cell surface molecule binding portion and a B cell surface molecule. One of the catalytic products of the growth factor precursor of the present invention is a growth factor capable of inducing B cell mitogenesis.

The growth factor precursor of the present invention may be synthesised as a single polypeptide chain. The polypeptide chain comprises various regions such as a component of the variable heavy chain and a component of a variable light chain of an immunoglobulin (referred to herein as variable light chain and variable heavy chain domains), a target antigen, a T cell surface molecule binding portion and at least one B cell surface molecule binding portion. Additional regions may also be included such as purification tags including FLAG and hexa-his and a molecular adjuvant such as but not limited to C3d, CTLA4 and/or CD40L. Such a polypeptide may be produced from fusing together a series of nucleotide sequences to produce a single nucleic acid molecule which, when expressed in an appropriate host cell, produces a single amino acid sequence in the form of the polypeptide.

Alternatively, the polypeptide chain may be made in modular form and the modules bound, ligated, linked or otherwise associated together. For example, the growth factor precursor may comprise a multimodular molecule having a module comprising a B cell surface molecule binding portion, a module comprising a T cell surface molecule binding portion, and one or more modules comprising the variable heavy chain domain and variable light chain domain.

The modular components may be bound, ligated or otherwise associated together by any convenient means such as but not limited to peptide bonding, electrostatic attraction, covalent bonding, di-sulphide bridges and/or hydrogen binding. A combination of covalent and peptide bonding and disulphide bridging are particularly preferred in forming a growth factor precursor from the modules.

The growth factor of the present invention functions after catalytic processing. Where the growth factor precursor comprises two B cell surface molecule binding portions, the masking effect of the variable heavy and light chains may be in respect of both B cell surface molecule binding portions or only one B cell surface molecule binding portion. Where the growth factor precursor molecule comprises only one B cell surface molecule binding portion then a multimerizing inducing unit or multimer forming portion may also be included in order to form multimers of the B cell surface molecule binding portion of the growth factor.

In a related aspect, the present invention provides a growth factor precursor comprising a recombinant polypeptide chain or a molecule having modular peptide components or a synthetic equivalent thereof wherein said polypeptide chain or modular peptide molecule comprises at least one B cell surface molecule binding portion, at least one T cell surface molecule binding portion capable of providing T cell dependent help to a B cell, an antigen cleavable by a catalytic antibody and a peptide portion comprising domains from both a variable heavy chain and a variable light chain of an immunoglobulin and wherein said variable heavy chain and variable light chain domains in the growth factor precursor, associate together by intra- and/or inter-domain bonding and substantially prevent the at least one B cell surface molecule binding portion from interacting with a B cell surface molecule such that upon cleavage of said antigen by a catalytic antibody, the peptide comprising said variable heavy chain and variable light chain domain permits the at least one B cell surface molecule binding portion to interact with a B cell surface molecule.

The T cell surface molecule binding portion provides T cell dependent help for the B cell. The T cell surface molecule binding portion is preferably part of the growth factor precursor but may alternatively be exogenously supplied. An example of an exogenously supplied portion having T cell dependent help from a B cell is anti-CD40L antibodies or functional equivalents thereof.

In a further aspect of the present invention, the multimizing inducing portion comprises a signal peptide such as from the outer membrane protein A (ompA) or a functional equivalent or derivative thereof linked preferably to the C-terminal portion of the growth factor.

In a particularly preferred embodiment, the B cell surface molecule binding portions comprises a B cell surface binding portion such as a B cell surface immunoglobulin although the present invention extends to a range of B cell surface molecules the binding, interaction and/or cross-linking of which leads to or facilitates B cell mitogenesis.

The present invention further contemplates a composition of matter capable of inducing B cell mitogenesis of a catalytic B cell after catalytic processing said composition of matter comprising components selected from:

(i) a recombinant or synthetic molecule capable of inducing a B cell surface molecule binding portion in multimeric form;

(ii) a recombinant or synthetic molecule of (i) comprising a further portion providing a T cell surface molecule binding portion; and (iii) separate compositions mixed prior to use or used sequentially or simultaneously comprising in a first composition a component having a B cell surface molecule binding portion and in a second composition a molecule capable of providing a T cell surface molecule binding portion;

said composition of matter further comprising a recombinant or synthetic B cell surface molecule binding portion masked by components of a variable heavy chain domain and a variable light chain domain which variable heavy and light chains are associated together by intra- and/or inter-domain bonding.

In a related embodiment, the present invention is directed to a composition of matter capable of inducing B cell mitogenesis of catalytic B cells after catalytic processing said composition of matter comprising components selected from:

(i) a recombinant or synthetic molecule comprising a B cell surface molecule binding portion;

(ii) a recombinant or synthetic molecule comprising a B cell surface molecule binding portion and a signal peptide linked to the C-terminal portion of the B cell surface molecule binding portion;

(iii) a recombinant or synthetic molecule of (i) or (ii) comprising a further portion providing a T cell surface molecule binding portion; and (iv) separate compositions mixed prior to use or used sequentially or simultaneously comprising in a first composition a component having a B cell surface molecule binding portion and in a second composition a molecule capable of providing a T cell surface molecule binding portion;

said composition of matter further comprising a recombinant or synthetic B cell surface molecule binding portion masked by components of a variable heavy chain domain and a variable light chain domain which variable heavy and light chains are associated together by intra- and/or inter-domain bonding.

Preferably, for example to facilitate cross-linking of B cell surface molecules to induce mitogenesis (i.e. activation and proliferation), the growth factor comprises at least two B cell surface molecule binding portions. Alternatively, where the growth factor is present in multimeric form or is capable of being presented in multimeric form, the molecule may comprise a single B cell surface molecule binding portion.

The presentation of a T cell surface molecule binding portion on the surface of a B cell allows for B cell mitogenesis. The term "B cell mitogenesis" is used herein in its broadest context and includes B cell activation and proliferation, clonal expansion, affinity maturation and/or antibody secretion as well as growth and differentiation.

In accordance with the present invention, a multimer comprises two or more growth factor molecules or a precursor thereof. Examples of portions inducing multimerisation include but are not limited to an antibody, a region facilitating formation of cross-linked molecules or a signal peptide. Cross-linkage in this context includes any interaction that provides bonding adequate to lead to multimer formation including but not limited to covalent linkage, ionic linkage, lattice association, ionic bridges, salt bridges and non-specific molecular association. A particularly preferred embodiment of the present invention is directed to the use of a signal peptide such as the signal peptide of ompA [Skerra, *Gene*, 151: 131–135, 1994] or a functional derivative thereof. A "functional derivative" in this context is a mutant or derivative of the ompA signal peptide (or its functional equivalent) which still permits multimer formation of the growth factor.

An example of a suitable B cell surface molecule binding portion is protein L from *Peptostreptococcus magnus*. Protein L has five immunoglobulin-binding domains. Other immunoglobulin binding molecules include protein A, protein G and protein H. The present invention, however, extends to any molecule capable of binding to a B cell surface component including, for example, a ligand of a B cell receptor.

The portion of the recombinant or synthetic molecule defining a T cell surface molecule binding portion is presented to a preferably already primed T cell to induce B cell proliferation and affinity maturation of an antibody in the germinal centre. This is generally accompanied by immunoglobulin class switching and antibody secretion into the serum. Generally, the T cell surface molecule binding portion is internalised within the B cell and presented on major histocompatibility complex (MHC) class II.

An example of a T cell surface molecule binding portion is from hen egg lysozyme (HEL) [Altuvia et al, *Molecular Immunology*, 31. 1–19, 1994] or is a derivative thereof such as a peptide comprising amino acids 42 to 62 from HEL or a homologue or analog thereof. This T cell surface molecule binding portion is recognised by the T cell receptor (TCR) of HEL specific T cells when presented by an antigen presenting cell (APC) on the MHC class II molecule H-2A$^\kappa$ in mice or other MHC class II molecules or their equivalents in other mammals such as humans. Examples of other T cell surface molecule binding portions include but are not limited to tetanus toxoid, ovalbumin, malarial antigens as well as other regions of HEL. One skilled in the art would readily be able to select an appropriate T cell surface molecule binding portion.

In an alternative embodiment, the portion providing the T cell surface molecule binding portion functions like a T cell epitope. An example of such a portion is an anti-CD40L antibody.

As stated above, the B cell surface molecule binding portions induce B cell activation and blast formation. The internalisation and processing of the growth factor leads to the presentation of the antigen on MHC II. T cell recognition of MHC II with the antigen signals the activated B cell to proliferate and undergo antibody class switching and secretion.

The mitogenic growth factor of the present invention is most useful in generating antibodies of desired catalytic specificity when, in a precursor form, it selects "catalytic" B cells. The precursor growth factor comprises a target antigen to which a catalytic antibody is sought and contains components which mask antigen-independent clonal expansion of B cells. Upon cleavage of the antigen by a selected B cell surface immunoglobulin, the growth factor can induce B cell mitogenesis.

In effect, then B cells are selected on the catalytic activity of their surface immunoglobulin rather than on their birding to a transition state analog. This allows for affinity maturation in the germinal centres and ensures "catalytic-maturation" to obtain the highest enzymatic turn-over rate possible in vivo. This aspect of the present invention is achieved by designing growth factor precursor shielded and substantially inactive until released through cleavage by a catalytic antibody on a B cell surface. The term "cleavage" in this context is not limiting to the breaking of bonds but includes an interaction adequate to remove or reduce shielding of the B cell growth factor.

The liberated growth factor activates the catalytic B cell via the B cell surface molecule binding portion domains. The growth factor is then internalised and processed analogous to a normal antigen. Intracellular processing permits the T cell surface molecule binding portion being presented on the B cell surface and this leads to T cell dependent clonal expansion of the B cell as well as catalytic maturation and secretion of the catalytic antibody. The catalytic antibodies can then be detected in serum and "catalytic" B cells can be recovered by standard techniques.

The antigen according to this aspect of the present invention is any antigen to which a catalytic antibody is sought. Examples include cytokines such as but not limited to tumor necrosis factor (TNF), an interleukin (IL) such as IL-1 to IL-15, interferons (IFN) such as IFNα, IFNβ or IFNγ, colony-stimulating factors (CSF) such as granulocyte colony-stimulating factor (G-CSF), granulocyte-macrophase colony-stimulation factor (GM-CSF), blood factors such as Factor VIII, erythropoietin and haemopoietin, cancer antigens, docking receptors from pathogenic viruses such as HIV, influenza virus or a hepatitis virus (eg. HEP A, HEP B, HEP C or HEP E) and amyloid plaques such as in Alzheimer's disease patients or myeloma patients. More particularly, in the case of TNF, proteolytic inactivation of TNF would be useful in the treatment of rheumatoid arthritis and toxic shock syndrome. By targeting viral docking receptors, pathogenic viruses such as HIV, hepatitis viruses and influenza viruses are rendered effectively inactive. Catalytic antibodies will also be useful in the clearance of amyloid plaques in Alzheimer's disease or myeloma disease patients. Targeting IgE, for example, may provide a mechanism for treating inflammatory conditions such as asthma.

The catalytic antibodies of the present invention may also be useful in detoxifying drugs such as drugs consumed by an individual. For example, the effects of cannabis or heroin or other drugs could be treated in an individual by the administration of catalytic antibodies directed to the active components of those drugs (Mets el al. *Proc. Natl. Acad. Sci. USA* 95: 10176–10181, 1998). Furthermore, catalytic antibodies may be useful in the treatment of autoimmune and inflammatory disease conditions such as by targeting autoimmune antibodies. Catalytic antibodies also have a use in environmental and other industrial situations and could be directed to environmental pollutants such as petroleum products and plastics. In all these situations, suitable antigens would be selected and incorporated into the growth factor precursor of the present invention.

In a related aspect of the present invention, the "antigen" portion of the growth factor precursor can be mimicked by a target site such as an amino acid linker sequence comprising a protease cleavage site. Examples include an amino acid linker sequence comprising the tabacco etch virus (TEV) protease cleavage site. More particularly, in the case of a TEV protease cleavage site, cleaving of the amino acid linker sequence by the TEV protease would be useful for producing characteristics similar to those of a catalytic antibody. This provides a useful model system for developing growth factor molecules.

The growth factor precursor enables an antigen to be recognised by a B cell via a growth factor capable of inducing B cell mitogenesis. The growth factor is in "precursor" form until cleavage of all or part of the antigen. It is important, however, that the B cell surface molecule binding portions be "masked" until catalytic B cells induce cleavage of the target antigen and exposure of the B cell surface molecule binding portions. Masking is provided by molecules capable of binding to or otherwise associating with the B cell surface molecule binding portion. In a particularly preferred embodiment, the masking molecules are all or a portion of the variable heavy chain domain and variable light chain domain of an immunoglobulin.

In a particularly preferred embodiment, a fragment comprising a variable heavy and light chain (Fv domains) is employed which is a single chain (sc) and/or disulphide stabilized (ds). The scdsFV fragment is conveniently obtainable from plasmacytoma McPc603, described in (Freund et al. *Biochemistry*, 33: 3296–3303, 1994). The variable light and heavy chain regions are preferably present as a single amino acid sequence. The regions fold and associate together by inter-domain attractive forces. Intra-domain attractive forces may also be involved. Preferably, the intra- and inter-domain attractive forces are disulphide bonds but the present invention extends to other forces capable of stabilising the domains such that they fold over or are in close proximity to at least one B cell surface molecule binding portion thus preventing B cell surface molecule binding portion interaction with a B cell surface molecule. Reference to inter- and intra-domain bonding means bonding with the polypeptide chain of the growth factor precursor and not to bonding between different polypeptide chains.

Accordingly, another aspect of the present invention is directed to a growth factor precursor comprising a recombinant polypeptide chain or a molecule having modular peptide components or a synthetic equivalent thereof wherein said polypeptide chain or modular peptide molecule comprises at least one B cell surface molecule binding portion, at least one T cell surface molecule binding portion capable of providing T cell dependent help to a B cell, an antigen cleavable by a catalytic antibody and a peptide portion comprising domains from both a variable heavy chain and a variable light chain of an immunoglobulin and wherein said variable heavy chain and variable light chain domains in the growth factor precursor, associate together by intra- and/or inter-domain bonding and substantially prevent the at least one B cell surface molecule binding portion from interacting with a B cell surface molecule such that upon cleavage of said antigen by a catalytic antibody, the peptide comprising said variable heavy chain and variable light chain domain permits the at least one B cell surface molecule binding portion to interact with a B cell surface molecule.

In a related embodiment, the present invention provides a growth factor precursor comprising a recombinant polypeptide chain or a molecule having modular peptide components or a synthetic equivalent thereof wherein said polypeptide chain or modular peptide molecule comprises at least one B cell surface molecule binding portion, at least one T cell surface molecule binding portion capable of providing T cell dependent help to a B cell, an antigen cleavable by a catalytic antibody and a peptide portion comprising domains from both a variable heavy chain and a variable light chain of an immunoglobulin and wherein said variable heavy chain and variable light chain domains in the growth factor precursor associate together by intra- and/or inter-domain bonding and substantially prevent the at least one B cell surface molecule binding portion from interacting with a B cell surface molecule such that upon cleavage of said antigen by a catalytic antibody, the peptide comprising said variable heavy chain and variable light chain domain permits the at least one B cell surface molecule binding portion to interact with a B cell surface molecule wherein if said growth factor precursor comprises a single B cell surface molecule binding portion, then the growth factor precursor further comprises a multimerising inducing element.

Another aspect of the present invention provides a growth factor precursor comprising a recombinant polypeptide chain or a molecule having modular peptide components or a synthetic equivalent thereof wherein said polypeptide chain or modular peptide molecule comprises at least two B cell surface molecule binding portions, an antigen cleavable by a catalytic antibody and a peptide portion comprising domains from both a variable heavy chain and a variable light chain such that in the growth factor precursor, these variable chain components associate together by intra- and/or inter-domain disulphide bridges and, when associated together, substantially prevent at least one of the B cell surface molecule binding portions from interacting with a B cell surface ligand for said epitope wherein upon cleavage of said antigen by a catalytic antibody, the at least two B cell surface molecule binding portions induce activation and proliferation of a B cell expressing said catalytic antibody.

A particularly useful masking molecule is derived from the variable heavy and light chain of McPc603. The latter molecule is expressed in the periplasmic space of DH10B and can be purified on an L-column. The variable heavy and light chain components is preferably present on a single peptide chain.

In a particularly preferred embodiment, the recombinant or synthetic growth factor precursor substantially prevents binding of at least one B cell surface molecule binding portion to a cognate B cell surface immunoglobulin thereby preventing B cell activation by having immunoglobulin peptide(s) or chemical equivalents thereof linked, fused or otherwise associated with the growth factor precursor to facilitate masking of the B cell activating effects of the growth factor. In a particularly preferred embodiment, the precursor comprises an antigen to which a catalytic antibody is sought and portions capable or masking a B cell surface molecule binding portionon the growth factor precursor. The precursor preferably contains domains for variable heavy and light chain components which associate together and exhibit inter- and intra-domain disulphide bridges.

Generally, the immunoglobulin molecules which bind to the B cell surface molecule binding portion of the growth factor are linked to the N-terminal and/or C-terminal portions of the growth factor. For example, one particularly preferred embodiment of the present invention provides a growth factor precursor comprising the structure:

$$I'AX_1[X_2]_d[X_3]_a[A]_rI''$$

wherein:

X$_1$ and X$_3$ are B cell surface molecule binding portions;

d is 0 or 1 or >1;

a is 0 or 1 or >1;

I' and I" are either both present or only one is present and they may be the same or different and each is a blocking reagent for X$_1$ and/or X$_3$ such as a variable heavy and light chain or a sc-ds-Fv molecule;

A is the target antigen for which a catalytic antibody is sought;

X$_2$ is an entity providing T cell dependent help to a B cell; and r is 0, 1 or >1, wherein a catalytic antibody on the surface of said 1 cell is capable of cleaving all or part of A from said recombinant or synthetic molecule resulting in the molecule $[A']X_1X_2[X_3]_a$ [A'] wherein A' is optionally present and is a portion of A after cleavage with the catalytic antibody wherein said resulting molecule is capable of inducing T cell dependent B cell mitogenesis of the B cell to which X$_1$ and X$_3$ bind.

The molecular components of I' AX$_1$X$_2$X$_3$A I" may be in any sequence order.

In another embodiment, the I'AX$_1$X$_2$X$_3$A I" molecule or part thereof may be in multimeric form. This is particularly the case when all or part of the molecule includes a multimerisation component (M) such as but not limited to the signal peptide of ompA. The monomeric units may be bound or otherwise associated together by any number of binding means such as contemplated above including covalent bonding, salt bridges, disulphide bridges and hydrophobic interactions amongst many others. Depending on the extent of multimerisation, this may impair the masking ability of B cell surface molecule binding domains of the growth factor and some antigen-independent clonal expansion may occur. This may not be too disadvantageous where there is at least some catalytic antibody dependent B cell mitogenesis.

According to this embodiment, there is provided a growth factor precursor comprising the structure:

$$[I'AX_1[X_2']_o[X_2X_3[A]_pI'']_n]_m$$

wherein:

I' and I" are both present or only one is present and each is a blocking reagent for X$_1$ and/or X$_3$ such as a variable heavy or light component or an sc-ds-Fv;

A is the target antigen for which a catalytic antibody is sought;

X$_1$ and X$_3$ are B cell surface molecule binding portions;

X$_2$ and X$_2$' may be the same or different and each is an entity capable or providing T cell dependent help for a B cell;

o may be 0 or 1;

p may be 0 or 1;

n indicates the multimeric nature of the component in parentheses and may be 0, 1 or >1;

m indicates the multimeric nature of the component in parenthesis and may be 1 or >1.

Preferably, n and m are each from about 1 to about 10,000 more preferably from about 1 to about 1,000 and still more preferably from about 1 to about 200.

Preferably, if n is 0, then o is 1.

In alternative embodiments, the growth factor precursor comprises the structure $[[I'AX_2X_3]_n[X_2']_o[X_1'AI'']_m$ or $[[I'AX_1[X_2']_o]_n][X_2X_3AI'']_m]$ The exact number ascribed to n and m may not be ascertainable but the multimeric nature identified functionally or physically by size (eg. determined using HPLC or PAGE).

The present invention is now described by way of example only with reference to a particular growth factor precursor analogue. This analogue is capable of mimicing a growth factor precursor but uses an enzyme sensitive molecule in place of the antigen. Such an analogue is a useful model for designing growth factor precursors.

The growth factor precursor analogue comprises modular components linked together by a glycine-serine bridge referred to as [ggggs]$_4$. The unit is present four times. It is abbreviated herein "g". Two B cell surface molecule binding portions, L, are linked by a g bridge to form the core L-g-L. On the carboxy end of the B cell surface molecule binding portion, a hexa-his Tag is linked to form: L-g-L-6xHis. The N terminal end of the molecule comprises a TEV protease cleavage site to provide the molecule:

TEV-L-g-L-6xHis.

The blocking or masking region is provided by a single chain molecule comprising portion of a variable heavy chain and a variable light chain of McPc603. The variable portions associate together and are stabilised by inter- and intra-domain disulphide bridges. These mask at least one of the B cell surface molecule binding portions on L. The molecule may alternatively only comprise a single L.

In the formula:

$$[I'AX_1[X_2']_o[X_2\ X_3[A]_p I'']_n]_m,$$

I' and I" may both be present or one or other is present and represent a single amino acid sequence comprising a portion of the variable heavy and variable light chain of McPc603. Element A is the target antigen to which a catalytic antibody is sought. Element A may be present once or twice. Accordingly, p is 0 or 1. $X_1$ and $X_3$ are the B cell surface molecule binding portions. Two B cell surface molecule binding portions are preferred but one B cell surface molecule binding portion may surfice. In one embodiment, when the growth factor precursor carries a multimerizing component such as the ompA, signal peptide then the growth factor precursor may contain only a single epitope. In these cases, n is 0. $X_2$ and $X_2'$ are T cell surface molecule binding portions providing T cell dependent help for a B cell. If a single T cell surface molecule binding portion is present, o is 0. Where the growth factor precursor is in multimeric form n and m are >1 and up to about 10,000 and 200, respectively. The elements may be in any order.

The growth factor precursor of the present invention may also contain elements to assist in purification of the molecule. Examples include the hexa-His affinity tag and FLAG-tag. The g bridge is preferred but the present invention extends to any linking mechanism and is most preferably a flexible linking peptide.

In the example referred to above, TEV is the target site further TEV protease which mimics the cleavage by a catalytic antibody.

Another aspect of the present invention contemplates a nucleic acid molecule encoding the growth factor precursor herein described. According to this aspect of the present invention, there is provided a nucleic acid molecule comprising a sequence of nucleotides encoding or complementary to a sequence encoding a polypeptide chain or a molecule having modular peptide components or a synthetic equivalent thereof wherein said polypeptide chain or modular peptide molecule comprises at least one B cell surface molecule binding portion, at least one T cell surface molecule binding portion capable of providing T cell dependent help to a B cell, an antigen cleavable by a catalytic antibody and a peptide portion comprising domains from both a variable heavy chain and a variable light chain of an immunoglobulin and wherein said variable heavy chain and variable light chain components in the growth factor precursor, associate together by intra- and/or inter-domain bonding and, when associated together, substantially prevent the at least one B cell surface molecule binding portion from interacting with a B cell surface molecule such that upon cleavage of said antigen by a catalytic antibody, the peptide comprising said variable heavy chain and variable light chain component permits the at least one B cell surface molecule binding portion to interact with a B cell surface molecule.

The preferred nucleic acid molecule of the present invention encodes the growth factor precursor defined herein as ccMThgL having the amino acid sequence substantially as set forth in SEQ ID NO: 16. The present invention further contemplates molecules having growth factor precursor activity with an amino acid sequence with at least about 60% similarity to ccMTLgL. Alternative percentage similarities include at least about 70%, at least about 80% and at least about 90% or above similarity to SEQID NO: 16.

In a particularly preferred embodiment, the nucleic acid molecule comprising a nucleotide sequence substantially set forth in SEQ ID NO: 15 or a nucleotide sequence having at least 60% similarity thereto or a nucleotide sequence capable of hybridising thereto under low stringency conditions of 42° C. Reference herein to a low stringency at 42° C. includes and encompasses from at least about 1% v/v to at least about 15% v/v formamide and from at least about 1M to at least about 2M salt for hybridisation, and at least about 1M to at least about 2M salt for washing conditions. Alternative stringency conditions may be applied where necessary, such as medium stringency, which includes and encompasses from at least about 16% v/v to at least about 30% v/v formamide and from at least about 0.5M to at least about 0.9M salt for hybridisation, and at least about 0.5M to at least about 0.9M salt for washing conditions, or high stringency, which includes and encompasses from at least about 31% v/v to at least about 50% v/v formamide and from at least about 0.01M to at least about 0.15M salt for hybridisation, and at least about 0.01M to at least about 0.15M salt for washing conditions.

The term "similarity" as used herein includes exact identity between compared sequences at the nucleotide or amino acid level. Where there is non-identity at the nucleotide level, "similarity" includes differences between sequences which result in different amino acids that are nevertheless related to each other at the structural, functional, biochemical and/or conformational levels. Where there is non-identity at the amino acid level, "similarity" includes amino acids that are nevertheless related to each other at the structural, functional, biochemical and/or conformational levels. In a particularly preferred embodiment, nucleotide and sequence comparisons are made at the level of identity rather than similarity. Any number of programs are available to compare nucleotide and amino acid sequences. Preferred programs have regard to an appropriate alignment. One such program is Gap which considers all possible alignment and gap positions and creates an alignment with the largest number of matched bases and the fewest gaps. Gap uses the alignment method of Needleman and Wunsch (*J. Mol. Biol.* 48: 443–453, 1970). Gap reads a scoring matrix that contains values for every possible GCG symbol match. GAP is available on ANGIS (Australian National Genomic Information Service) at website http://mell.angis.org.au.

In a related embodiment, the present invention provides a nucleic acid molecule encoding the growth factor precursor herein described. According to this aspect of the present invention, there is provided a nucleic acid molecule comprising a sequence of nucleotides encoding or complementary to a sequence encoding a polypeptide chain or a molecule having modular peptide components or a synthetic equivalent thereof wherein said polypeptide chain or modular peptide molecule comprises at least one B cell surface molecule binding portion, at least one T cell surface molecule binding portion capable of providing T cell dependent help to a B cell, an antigen cleavable by a catalytic antibody and a peptide portion comprising domains from both a variable heavy chain and a variable light chain of an immunoglobulin and wherein said variable heavy chain and variable light chain components in the growth factor precursor, associate together by intra- and/or inter-domain bonding and, when associated together, substantially prevent the at least one B cell surface molecule binding portion from interacting with a B cell surface molecule such that upon cleavage of said antigen by a catalytic antibody, the peptide comprising said variable heavy chain and variable light chain component permits the at least one B cell surface molecule binding portion to interact with a B cell surface molecule wherein if said growth factor precursor comprises a single B cell surface molecule binding portion, then the growth factor precursor further comprises a multimerising inducing element.

In another embodiment, the present invention is directed to a nucleic acid molecule comprising a sequence of nucleotides encoding or complementary to a sequence encoding a polypeptide chain or a molecule having modular peptide components or a synthetic equivalent thereof wherein said polypeptide chain or modular peptide molecule comprises at least one B cell surface molecule binding portion, at least one T cell surface molecule binding portion capable of providing T cell dependent help to a B cell, an antigen cleavable by a catalytic antibody and a peptide portion comprising domains from both a variable heavy chain and a variable light chain of an immunoglobulin and wherein said variable heavy chain and variable light chain components in the growth factor precursor, associate together by intra- and/or inter-domain bonding and, when associated together, substantially prevent the at least one B cell surface molecule binding portion from interacting with a B cell surface molecule such that upon cleavage of said antigen by a catalytic antibody, the peptide comprising said variable heavy chain and variable light chain component permits the at least one B cell surface molecule binding portion to interact with a B cell surface molecule.

Preferably, the nucleic acid molecule is in form of a genetic "vaccine". In this regard, a genetic vaccine conveniently comprises the nucleic acid molecule in, for example, a viral vector or other suitable nucleic acid transferring medium. Generally, one or more pharmaceutically acceptable carriers and/or diluents are also included. The genetic vaccine is introduced to cells either directly (e.g. intramuscularly), or systemically or cells are removed from an individual, the genetic vaccine introduced into the cells and then the cells are returned to the individual or a genetically related individual. The nucleic acid in the genetic vaccine after introduction to cells is expressed to produce the growth factor precursor of the present invention.

In a particularly preferred embodiment, the nucleic acid molecule in the genetic vaccine further comprises a nucleotide sequence encoding a molecular adjuvant. Examples of suitable molecular adjuvants include CTLA4 (Boyle et al. *Nature* 392: 408–411, 1998), CD40L (Lane et al. *J. Exp. Med.* 177:1209–1213, 1993) and C3d (Dempsey et al. *Science* 27: 348–350, 1996; Lou and Kohler, *Naurve Biotechnology* 16: 458–462, 1998).

The present invention extends to recombinant polypeptides defining the growth factor precursor and further comprising a molecular adjuvant attached thereto.

Upon cleavage of the growth factor precursor by a catalytic antibody recognising the antigen (for example, a TNF peptide portion), the covalent linkage between the B cell surface molecule binding portion and the variable heavy and light domains is broken. The blocking variable chains will dissociate from the B cell surface molecule binding portion due to the relatively low affinity (~$10^{-7}$M) of individual domains for each other. This will release the mature growth factor which can bind to and crosslink the surface immunoglobulin.

Catalytic antibodies can be detected in the serum using any number of procedures such as ELISA based assays and catalytic B cells may be recovered with standard hybridoma technology. Where the catalytic antibodies are from non-human animals, these can be humanised by recombinant DNA technology and produced for therapeutical applications in humans. Alternatively, the antibodies may be generated in a "humanized" animal such as a humanized mouse which is transgenic for the human Ig loci.

The present invention contemplates derivatives of the growth factor and/or its precursor. A derivative includes a mutant, part, fragment, portion, homologue or analogue of the growth factor and/or precursor or any components thereof. Derivatives to amino acid sequences include single or multiple amino acid substitutions, deletions and/or additions. Particularly useful derivatives include chemical analogues of the growth factor precursor and/or its components. Such chemical analogues may be useful in stabilizing the molecule for therapeutic, diagnostic and industrial use.

Analogues of the growth factor precursor contemplated herein include, but are not limited to, modification to side chains, incorporating of unnatural amino acids and/or their derivatives during peptide, polypeptide or protein synthesis and the use of crosslinkers and other methods which impose conformational constraints on the proteinaceous molecule or their analogues.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acid, contemplated herein is shown in Table 1.

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

The present invention further contemplates chemical analogues of the growth factor precursor capable of acting as antagonists or agonists of same. These may be useful in controlling the immunological response. Chemical analogues may not necessarily be derived from the growth factor precursor but may share certain conformational similarities. Alternatively, chemical analogues may be specifically designed to mimic certain physiochemical properties of the growth factor precursor. Chemical analogues may be chemically synthesised or may be detected following, for example, natural product screening of, for example, coral, soil, plants, microorganisms, marine invertebrates or seabeds. Screening of synthetic libraries is also contemplated by the present invention.

TABLE 1

| Non-conventional amino acid | Code |
|---|---|
| α-aminobutyric acid | Abu |
| α-amino-α-methylbutyrate | Mgabu |
| aminocyclopropane-carboxylate | Cpro |
| aminoisobutyric acid | Aib |
| aminonorbornyl-carboxylate | Norb |
| cyclohexylalanine | |
| cyclopentylalanine | Cpen |
| D-alanine | Dal |
| D-arginine | Darg |
| D-aspartic acid | Dasp |
| D-cysteine | Dcys |
| D-glutamine | Dgln |
| D-glutamic acid | Dglu |
| D-histidine | Dhis |
| D-isoleucine | Dile |
| D-leucine | Dleu |
| D-lysine | Dlys |
| D-methionine | Dmet |
| D-ornithine | Dorn |
| D-phenylalanine | Dphe |
| D-proline | Dpro |
| D-serine | Dser |
| D-threonine | Dthr |
| D-tryptophan | Dtrp |
| D-tyrosine | Dtyr |

TABLE 1-continued

| Non-conventional amino acid | Code |
|---|---|
| D-valine | Dval |
| D-α-methylalanine | Dmala |
| D-α-methylarginine | Dmarg |
| D-α-methylasparagine | Dmasn |
| D-α-methylaspartate | Dmasp |
| D-α-methylcysteine | Dmcys |
| D-α-methylglutamine | Dmgln |
| D-α-methylhistidine | Dmhis |
| D-α-methylisoleucine | Dmile |
| D-α-methylleucine | Dmleu |
| D-α-methyllysine | Dmlys |
| D-α-methylmethionine | Dmmet |
| D-α-methylornithine | Dmorn |
| D-α-methylphenylalanine | Dmphe |
| D-α-methylproline | Dmpro |
| D-α-methylserine | Dmser |
| D-α-methylthreonine | Dmthr |
| D-α-methyltryptophan | Dmtrp |
| D-α-methyltyrosine | Dmty |
| D-α-methylvaline | Dmval |
| D-N-methylalanine | Dnmala |
| D-N-methylarginine | Dnmarg |
| D-N-methylasparagine | Dnmasn |
| D-N-methylaspartate | Dnmasp |
| D-N-methylcysteine | Dnmcys |
| D-N-methylglutamine | Dnmgln |
| D-N-methylglutamate | Dnmglu |
| D-N-methylhistidine | Dnmhis |
| D-N-methylisoleucine | Dnmile |
| D-N-methylleucine | Dnmleu |
| D-N-methyllysine | Dnmlys |
| N-methylcyclohexylalamine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α-methylhistidine | Mhis |
| L-α-methylisoleucine | Mile |
| L-α-methylleucine | Mleu |
| L-α-methylmethionine | Mmet |
| L-α-methylnorvaline | Mnva |
| L-α-methylphenylalanine | Mphe |
| L-α-methylserine | Mser |
| L-α-methyltryptophan | Mtrp |
| L-α-methylvaline | Mval |
| N-(N-(2,2-diphenylethyl) carbamylmethyl)glycine | Nnbhm |
| L-N-methylalanine | Nmala |
| L-N-methylarginine | Nmarg |
| L-N-methylasparagine | Nmasn |
| L-N-methylaspartic acid | Nmasp |
| L-N-methylcysteine | Nmcys |
| L-N-methylglutamine | Nmgln |
| L-N-methylglutamic acid | Nmglu |
| Chexa L-N-methylhistidine | Nmhis |
| L-N-methylisolleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methylnorvaline | Nmnva |
| L-N-methylornithine | Nmorn |
| L-N-methylphenylalanine | Nmphe |
| L-N-methylproline | Nmpro |

TABLE 1-continued

| Non-conventional amino acid | Code |
|---|---|
| L-N-methylserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl-γ-aminobutyrate | Mgabu |
| α-methylcyclohexylalanine | Mchexa |
| α-methylcylcopentylalanine | Mcpen |
| α-methyl-a-napthylalanine | Manap |
| α-methylpenicillamine | Mpen |
| N-(4-aminobutyl)glycine | Nglu |
| N-(2-aminoethyl)glycine | Naeg |
| N-(3-aminopropyl)glycine | Norn |
| N-amino-α-methylbutyrate | Nmaabu |
| α-napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |
| N-(carboxymethyl)glycine | Nasp |
| N-cyclobutylglycine | Ncbut |
| N-cycloheptylglycine | Nchep |
| N-cyclohexylglycine | Nchex |
| N-cyclodecylglycine | Ncdec |
| N-cylcododecylglycine | Ncdod |
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(3-guanidinopropyl)glycine | Narg |
| N-(1-hydroxyethyl)glycine | Nthr |
| N-(hydroxyethyl))glycine | Nser |
| N-(imidazolylethyl))glycine | Nhis |
| N-(3-indolylethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylthreonine | Dnmthr |
| N-(1-methylethyl)glycine | Nval |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomophenylalanine | Mhphe |
| N-(2-methylthioethyl)glycine | Nmet |
| L-α-methyllysine | Mlys |
| L-α-methylnorleucine | Mnle |
| L-α-methylornithine | Morn |
| L-α-methylproline | Mpro |
| L-α-methylthreonine | Mthr |
| L-α-methyltyrosine | Mtyr |
| L-N-methylhomophenylalanine | Nmhphe |
| N-(N-(3,3-diphenylpropyl) carbamylmethyl)glycine | Nnbhe |
| 1-carboxy-1-(2,2-diphenyl-ethylamino)cyclopropane | Nmbc |

Other derivatives contemplated by the present invention include a range of glycosylation variants from a completely unglycosylated molecule to a modified glycosylated molecule. Altered glycosylation patterns may result from expression of recombinant molecules in different host cells.

Still a further aspect of the present invention extends to a method for producing catalytic antibodies to a specific antigen, said method comprising administering to an animal an effective amount of a growth factor precursor comprising an antigen capable of interacting with a B cell bound catalytic antibody said antigen linked to or otherwise associate with a B cell surface molecule binding portion and a portion capable of providing T cell dependent help to a B cell. The growth factor precursor further comprises a B cell surface molecule binding portion masking entity such as a portion of a variable heavy and light chain linked to the antigen.

Alternatively, the growth factor precursor may comprise a B cell surface molecule binding portion in multimeric form linked to an antigen for which a target antibody is sought. The portion providing T cell dependent help is preferably a T cell surface molecule binding portion and is preferably part of the precursor. However, it may be a separate entity administered simultaneously or sequentially to an animal. Again, the B cell surface molecule binding portion is masked as above.

The present invention also provides catalytic antibodies produced by the above method. Such catalytic antibodies may be directed to any antigen such as but not limited to a cytokine, for example, tumor necrosis factor (TNF), an interleukin (IL) such as IL-1 to IL-15, interferons (IFN) such as IFNα, IFNβ or IFNγ, colony-stimulating factors (CSF) such as granulocyte colony-stimulating factor (G-CSF), granulocyte-macrophage colony-stimulation factor (GM-CSF), blood factors such as Factor VIII, erythropoietin and haemopoietin, cancer antigens, docking receptors from pathogenic viruses such as HIV, influenza virus or a hepatitis virus (eg. HEP A, HEP B, HEP C or HEP E) and amyloid plaques such as in Alzheimer's disease patients or myeloma patients.

The catalytic antibodies of the present invention have particular therapeutic and diagnostic uses especially in relation to mammalian and more particularly human disease conditions.

Accordingly, the present invention contemplates a pharmaceutical composition comprising a growth factor precursor or a derivative thereof and optionally a modulator of growth factor precursor activity and one or more pharmaceutically acceptable carriers and/or diluents. More particularly, the pharmaceutical composition comprises catalytic antibodies generated by the growth factor precursor of the present invention. These components are hereinafter referred to as the "active ingredients".

The pharmaceutical forms suitable for injectable use include sterile aqueous solutions (where water soluble) or sterile powders for the extemporaneous preparation of sterile injectable solutions. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The preventions of the action of microorganisms can be brought about by various antibacterial and antifungal agents, for example, parabens, chlorobutanol, phenol, sorbic acid, thimersal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by sterilization such as by filtration. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that an oral dosage unit form contains between about 0.1 ng and 2000 mg of active compound, preferably between about 0.1 $\mu$g and 1500 mg and more preferably between about 1 $\mu$g and 100 mg.

The tablets, troches, pills, capsules and the like may also contain the components as listed hereafter a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry, orange or mango. Of course, any material used in preparing any dosage unit form should be pharmaceutically pure and substantially non-toxic in the amounts employed. In addition, the active compound(s) may be incorporated into sustained-release preparations and formulations.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions. These may include immune potentiating molecules, multimer facilitating molecules and pharmaceutically active molecules chosen on the disease conditions being treated.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from 0.1 ng to about 2000 mg, more preferably ranging from 0.1 $\mu$g and 1500 mg and even more preferably ranging between 1 $\mu$g and 1000 mg. Expressed in proportions, the active compound is generally present in from about 0.5 $\mu$g to about 2000 mg/ml of carrier. In the case of compositions containing supplementary active ingredients, the dosages are determined by reference to the usual dose and manner of administration of the said ingredients.

Still another aspect of the present invention is directed to antibodies to the growth factor precursor and its derivatives. Such antibodies may be monoclonal or polyclonal and are independent to the catalytic antibodies selected by the precursor. The (non-catalytic) antibodies to recombinant or synthetic the growth factor precursor or its derivatives of the present invention may be useful as therapeutic agents but are particularly useful as diagnostic agents. Antibodies may also be generated to the catalytic antibodies generated by the growth factor precursors. All these antibodies have particular application in diagnostic assays for the growth factor or catalytic antibody inducer thereof.

For example, specific antibodies can be used to screen for catalytic antibodies. The latter would be important, for example, as a means for screening for levels of these antibodies in a biological fluid or for purifying the catalytic antibodies. Techniques for the assays contemplated herein are known in the art and include, for example, sandwich assays and ELISA.

It is within the scope of this invention to include any second antibodies (monoclonal, polyclonal or fragments of antibodies or synthetic antibodies) directed to the antibodies discussed above. Both the first and second antibodies may be used in detection assays or a first antibody may be used with a commercially available anti-immunoglobulin antibody.

Both polyclonal and monoclonal antibodies are obtainable by immunization with the enzyme or protein and either type is utilizable for immnunoassays. The methods of obtaining both types of sera are well known in the art. Polyclonal sera are less preferred but are relatively easily prepared by injection of a suitable laboratory animal with an effective amount of antigen, or antigenic parts thereof, collecting serum from the animal, and isolating specific sera by any of the known immunoadsorbent techniques. Although antibodies produced by this method are utilizable in virtually any type of immunoassay, they are generally less favoured because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art.

Another aspect of the present invention contemplates a method for detecting an antigen in a biological sample from a subject said method comprising contacting said biological sample with an antibody specific for said antigen or its derivatives or homologues for a time and under conditions sufficient for an antibody-antigen complex to form, and then detecting said complex. In this context, the "antigen" may be a growth factor, its precursor, a component thereof or a catalytic antibody induced thereby.

The presence of antigen may be accomplished in a number of ways such as by Western blotting and ELISA procedures. A wide range of immunoassay techniques are available as can be seen by reference to U.S. Pat. Nos. 4,016,043, 4,424,279 and 4,018,653. These, of course, includes both single-site and two-site or "sandwich" assays of the non-competitive types, as well as in the traditional competitive binding assays. These assays also include direct binding of a labelled antibody to a target.

Sandwich assays are among the most useful and commonly used assays and are favoured for use in the present invention. A number of variations of the sandwich assay technique exist, and all are intended to be encompassed by the present invention. Briefly, in a typical forward assay, an unlabelled antibody is immobilized on a solid substrate and the sample to be tested brought into contact with the bound molecule. After a suitable period of incubation, for a period of time sufficient to allow formation of an antibody-antigen complex, a second antibody specific to the antigen, labelled with a reporter molecule capable of producing a detectable signal is then added and incubated, allowing time sufficient for the formation of another complex of antibody-antigen-labelled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of hapten. Variations on the forward assay include a simultaneous assay, in which both sample and labelled antibody are added simultaneously to the bound antibody. These techniques are well known to those skilled in the art, including any minor variations as will be readily apparent. In accordance with the present invention the sample is one which might contain an antigen including cell extract, supernatant fluid, tissue biopsy or possibly serum, saliva, mucosal secretions, lymph, tissue fluid and respiratory fluid. The sample is, therefore, generally a biological sample comprising biological fluid but also extends to fermentation fluid and supernatant fluid such as from a cell culture.

In the typical forward sandwich assay, a first antibody having specificity for the antigen or antigenic parts thereof, is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2–40 minutes, or overnight if more convenient) and under suitable conditions (e.g. from room tempterature to about 40° C. such as 25–37° C.) to allow binding of any subunit present in the antibody. Following the incubation period, the antibody subunit solid phase is washed and dried and incubated with a second antibody specific for a portion of the hapten. The second antibody is linked to a reporter molecule which is used to indicate the binding of the second antibody to the hapten.

An alternative method involves immobilizing the target molecules in the biological sample and then exposing the immobilized target to specific antibody which may or may not be labelled with a reporter molecule. Depending on the amount of target and the strength of the reporter molecule signal, a bound target may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules. In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable colour change. Examples of suitable enzymes include alkaline phosphatase and peroxidase. It is also possible to employ fluorogenic substrates, which yield a fluorescent product rather than the chromogenic substrates noted above. In all cases, the enzyme-labelled antibody is added to the first antibody hapten complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of hapten which was present in the sample. "Reporter molecule" also extends to use of cell agglutination or inhibition of agglutination such as red blood cells on latex beads, and the like.

Alternately, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic colour visually detectable with a light microscope. As in the EIA, the fluorescent labelled antibody is allowed to bind to the first antibody-hapten complex. After washing off the unbound reagent, the remaining tertiary complex is then exposed to the light of the appropriate wavelength the fluorescence observed indicates the presence of the hapten of interest. Immunofluorescene and EIA techniques are both very well established in the art and are particularly preferred for the present method. However, other reporter molecules, such as radioisotope, chemiluminescent or bioluminescent molecules, may also be employed.

The present invention may use any number of means to clone genetic sequences encoding catalytic antibodies. For example, a phage display library potentially capable of expressing a catalytic antibody on the phage surface may be used to screen for catalysis of defined antigens.

The present invention further contemplates the use of the products of catalysis of a growth factor precursor to induce B cell mitogenesis to generate catalytic antibodies to a specific antigen.

More particularly, the present invention contemplates the use of a growth factor precursor comprising an antigen to which a catalytic antibody is sought linked, fused or otherwise associated to a B cell surface molecule binding portion in the induction of B cell mitogenesis following catalytic cleavage of all or part of said antigen.

Still another embodiment of the present invention contemplates the use of an antigen linked, fused or otherwise associate to a B cell surface molecule binding portion in the manufacture of a growth factor precursor to induce B cell mitogenesis following catalytic cleavage of all or part of said antigen.

The present invention is further described by the following non-limiting examples.

EXAMPLE 1

GENERATION OF LHL FROM SYNTHETIC OLIGONUCLEOTIDES

LHL was generated from three overlapping synthetic oligos, a 115mer, a 116mer and a 105mer, using the proof-reading DNA polymerase Pfu in two 20 cycle PCR reactions. The two PCR products (290 bp and 200 bp) were purified and blunt end cloned into the expression vector pASK75. The sequence was verified by automated sequencing. All subsequent PCRs were done in a similar fashion as described in the literature. The nucleotide and corresponding amino acid sequence for LHL is shown in SEQ ID NO:1 and SEQ ID NO:2 respectively.

EXAMPLE 2

EXPRESSION OF LHL IN *E. COLI* AND PURIFICATION OVER A HUMAN IgG (huIgG) AFFINITY COLUMN

The expression vector pASK75 directs protein expression via the ompA signal peptide into the periplasm of *E. coli*. Protein expression was induced with 200 ng/ml anhydrotetracycline for 16 hrs in midlog *E. coli* DH10B cultures. Cells were lysed and soluble LHL purified (>95%) over a huIgG affinity column. Extensive washes with 0.5% v/v Triton X-100 were performed on the affinity column in order to eliminate endotoxins from the preparations. Expression levels were estimated at 20 mg per litre of culture.

EXAMPLE 3

GENERATION OF AN LHL PROTEIN CARRYING THE N-TERMINAL FLAG EPITOPE AND THE C-TERMINAL STREP-TAG

A form of LHL (referred to herein as "LHL.seq") was generated by PCR containing the FLAG epitope at its N-terminus and the so called strep-tag at its C-terminus. The nucleotide and corresponding amino acid sequence for LHL.seq is shown in SEQ ID NO:7 and SEQ ID NO:8, respectively. The FLAG epitope comprises the amino acids DYKDDDDK (SEQ ID NO:9) and the strep-tag the amino acids AWRHPQFGG (SEQ ID NO:14). The FLAG epitope is recognised by several anti-FLAG monoclonal antibodies and the strep-tag by streptavidin. The strep-tag was used for purification of LHL.seq over a streptavidin column. LHL.seq was washed with 0.5% v/v Triton X-100, Tween20 and PBS while bound to the column in order to minimise endotoxin levels. LHL.seq was eluted with either 100 mM glycine pH2.0 or with 1 mg/ml diaminobiotin in PBS. In this method LHL.seq was not purified on the basis of binding immunoglobulin, thereby eliminating potential contamination of other unknown bacterial proteins which also bind inmmunoglobulins. The biological activity of LHL.seq, however, remained identical to that of LHL. The FLAG-epitope was added to the N-terminus in order to facilitate the secretion of LHL.seq into the periplasmic space. As in previous expression studies, this was unsuccessful and LHL.seq needed to be purified from total bacterial lysate. As a result of this, the ompA signal peptide is not removed, which in turn led to formation of LHL.seq multimers.

EXAMPLE 4

MITOGENIC ACTIVITY OF LHL ON B CELLS

Mitogenic activity of LHL on B cells was tested in overnight cultures of splenocytes and mesenteric lymphocytes as well as on purified B cells. The activation status of B cells was analysed by FACS, examining B cell size and induction of B7-2 surface expression. LHL's activation potency is similar to LPS (10 $\mu$g/ml), a bacterial mitogenic lipopolysaccharide and anti-IgM antibody (25 $\mu$g/ml), which crosslinks surface IgM. The results have been independently obtained in several different mouse strain e.g. B10.A(4R), CBA, C3H/HeJ and BALB/c. B cells showed a clear dose response to LHL when titrated in 5-fold dilutions (25 $\mu$g/ml to 1.6 ng/ml) in the activation assay. Parallel experiments analysing the T cell activation status within the same cultures demonstrated that LHL has no effect on T cells. T cells did not show any blast formation nor did they upregulate activation markers, e.g. IL-2 receptor alpha chain (CD25).

EXAMPLE 5

BLOCKING OF LHL MITOGENICITY BY HuIgG

In the same experiments, soluble hulgG (500 $\mu$g/ml) which binds to the L domains was used to specifically block the activity of LHL. These results rule out that B cell activation was due to a contamination of the bacterially produced LHL with endotoxins.

EXAMPLE 6

PROCESSING OF LHL BY B CELLS AND PRESENTATION OF THE H EPITOPE TO THE HEL-SPECIFIC HYBRIDOMA 3A9

Splenocytes or mesenteric lymphocytes were cocultured with the T cell hybridoma 3A9 in the presence of LHL. 3A9 is specific for the HEL peptide 52–61aa presented on MHC II H-2A$^{K}$. Upon recognition of this peptide, 3A9 secretes IL-2. IL-2 production was measured in a bio assay which evaluates the proliferation of an IL-2 dependent cell line (CTLL) on the basis of $^{3}$H-thymidine incorporation during DNA synthesis. Presentation of H to 3A9 by B cells was clearly demonstrated by the proliferation of the CTLL and could be specifically blocked with huIgG.

EXAMPLE 7

GENERATION OF THE VARIABLE (V)-KAPPA LIGHT CHAIN ACCORDING TO THE HUMAN LEN PROTEIN SEQUENCE

The amino acid sequence of the gene encoding the human myeloma protein LEN was used to generate a variable kappa light chain. This human kappa light chain protein (hereinafter referred to as "kappa") is soluble at relatively high concentrations and has been shown to bind protein L. Kappa was generated from synthetic oligonucleotides by PCR. To facilitate protein purification, a FLAG epitope was added to the N-terminus and a strep-tag to the C-terminus. The nucleotide and amino acid sequence of kappa is shown in SEQ ID NO:10 and 11, respectively.

EXAMPLE 8

EXPRESSION OF KAPPA IN E.COLI DH10B

Kappa was cloned into pASK75, allowing inducible expression of kappa into the periplasmic space of E. coli. Expression was induced in logarithmically growing cultures of E. coli strain DH10B cells with 400 ng/ml of anhydro-tetracycline for >4 hrs.

EXAMPLE 9

PURIFICATION OF KAPPA PROTEIN FROM THE PERIPLASM OF DH10B

Cultures were spun down and resuspended in a buffer containing 400 mM sucrose on ice. After 20 min cells were pelleted. Kappa was then purified over an anti-FLAG and/or streptavidin column from the periplasmic fraction.

EXAMPLE 10

CONFIRMATION OF PROPER FOLDING OF KAPPA AFTER PURIFICATION

The proper folding of kappa was demonstrated by its capacity to bind LHL. Kappa was bound to the streptavidin column via its strep-tag. This kappa-loaded column was then shown to bind LHL. The non strep-tag carrying LHL did not bind to the streptavidin column alone.

EXAMPLE 11

GENERATION OF TLHL

TLHL was generated from LHL, kappa and synthetic oligonucleotides encoding a linker connecting kappa and LHL by PCR. The linker contained an amino acid sequence corresponding to the tobacco etch virus (TEV) protease recognition/cleavage site. All components were cloned into pASK75 resulting in the following protein sequence: FLAG-kappa-linker-TEV-LHL-streptag. Potentially, TLHL could show similar characteristics as CATAB, since one kappa binding site is blocked and two are required for surface immunoglobulin cross-linking. The nucleotide and amino acid sequences of TLHL are shown in SEQ ID NO:5 and SEQ ID NO:6, respectively.

EXAMPLE 12

EXPRESSION OF TLHL IN DH10B

TLHL expression was induced in logarithmically growing cultures by addition of 400 ng/ml anhydro-tetracycline for >4hrs. TLHL was not secreted into the periplasmic space and caused some cell lysis after induction.

EXAMPLE 13

PURIFICATION OF TLHL FROM TOTAL BACTERIAL LYSATE

TLHL was purified via its strep-tag over a streptavidin column from total bacterial lysate. Endotoxin levels were reduced using the washing protocol earlier described.

EXAMPLE 14

CLEAVAGE OF TLHL INTO "T" AND "LHL" WITH TEV

TLHL was designed so that the kappa portion of the protein could be cleaved off by the TEV protease. The TEV cleavage would generate two polypeptides, each of 172 amino acids. The identical size of the protein fragments is due to TLHL not being secreted into the periplasmic space of E. coli and, therefore, retaining the ompA signal peptide. Incubation of TLHL with the TEV protease in PBS at room temperature or at 4° C. produced therefore, a 19 kD band on an SDS-PAGE gel.

EXAMPLE 15

ASSEMBLY OF CATAB-TEV FROM TLHL AND KAPPA BY PCR

CATAB-TEV is assembled from TLHL and kappa by PCR. The TLHL and kappa can be linked by different peptides, for example, TNF amino acids 1–31, that are potential target sites for proteolytic antibodies. In this case, the linker includes a recognition sequence for the tobacco etch virus (TEV) protease which allows the generation of LHL from CATAB-TEV in vitro. The nucleotide and corresponding amino acid sequences of CATAB-TEV are shown in SEQ ID NO:3 and SEQ ID NO:4.

EXAMPLE 16

EXPRESSION OF CATAB IN DH10B AND PURIFICATION OVER A STREPTAVIDIN AFFINITY COLUMN VIA STREP-TAG

CATAB-TEV is expressed and purified in the same way as TLHL (see above).

EXAMPLE 17

DEMONSTRATION OF NON-MITOGENIC ACTIVITY OF CATAB-TEV ON B CELLS

CATAB-TEV is tested in the already established B cell assays which are used to analyse the mitogenic activity of LHL and LHL.seq.

EXAMPLE 18

REVELATION OF THE MITOGENIC ACTIVITY OF CATAB BY PROTEOLYTIC CLEAVAGE WITH TEV PROTEASE

Digestion of CATAB-TEV with the site specific protease from TEV cleaves the covalent bond between LHL and the kappa domains. This cleavage generates the mitogenic compound LHL which is tested in the standardised B cell activation assays.

EXAMPLE 19

USAGE OF CATAB IN SEVERAL MOUSE STRAINS OF THE K-HAPLOTYPE

Several mouse strains are immunised by different routes of administration, e.g. intra-splenic, in order to elicit a catalytic antibody response in vivo. The gld and lpr mutant strains are used as they have been shown to have a relatively high incidence of naturally occurring catalytic auto-antibodies, e.g. antibodies with DNAse activity.

EXAMPLE 20

DETECTION OF CATAB SPECIFIC CATALYTIC ANTIBODIES FROM THE SERUM

Serum antibodies from immunised mice are purified for example on a LHL affinity column. Purified antibodies may be incubated with 25I-labelled CATAB and the proteolytic cleavage is evaluated on PAGE gels. In addition, streptavidin may be used to immobilise CATAB via its C-terminal strep-tag on 96 well ELISA plates. Immobilised CATAB is proteolytically cleaved by incubation with purified catalytic serum antibodies and an N-terminal affinity tag, e.g. flag epitope, is lost. This loss is detected in a sandwich ELISA assay using horse radish peroxidase (HRPO) conjugated antibodies. B cells producing catalytic antibodies can be recovered by standard hybridoma techniques and the catalytic antibodies can be humanised by recombinant DNA technology. For example, "human" antibodies can be derived from humanized mice.

EXAMPLE 21

LHL.seq INDUCED B7-1 EXPRESSION

LHL.seq was tested for its ability to activate B cells as compared to stimulation with anti-IgM and anti-kappa. Activation status was measured by the induction of cell surface expression of the activation markers B7-1 and B7-2 and by entry of B cells into cell cycle. Levels of expression of B7-1 and B7-2 were determined by flow cytometry (FACS) with fluorescence-labelled monoclonal antibodies while entry into cell cycle was monitored by an increase in cell size by Forward Light Scatter (FSC).

The method employed was as follows. Mesenteric lymphnode cells from C3H/HeJ mice were centrifuged in Nycodenz (1.091 g/cm$^3$) to remove dead cells and red blood cells (rbc). This was followed by 1 hour adherence on plastic at 37° C. to remove adherent cells such as macrophages. Lymph node cells were stimulated in triplicate cultures 3×10$^5$/well in flat bottom 96-well plates in complete RPMI+ 10% FCS medium at 37° C. for 1–3 days. Upregulation of activation markers on B cells was monitored by gating on B220$^+$ Thy 1$^-$ cells to identify B cells. Stimulation with LPS (20 μg/ml), polyclonal F(ab)$_2$ anti-IgM antibodies (20 μg/ml) and anti-kappa antibodies (10 μg/ml) were included as controls. LHL.seq was used at 1 μg/ml. C3H/HeJ mice were used as source of lymphocytes since this particular mouse strain is non-responsive to LPS. The use of this strain in combination with the LPS control effectively precludes the possibility that B cell stimulation induced by LHL.seq were due to LPS (endotoxin) contamination of the bacterially expressed proteins.

FACS analysis showed that this two day stimulation of C3H/HeJ lymph node cells with LPS did not result in B cell activation whereas stimulation with either anti-IgM antibodies, anti-kappa antibodies or LHL.seq did as measured by an increased FSC and upregulation of B7-2. The characteristic potency of LHL.seq is demonstrated by the strong induction of B7-1 expression after incubation. Anti-IgM induces B7-1 on day 2–3 of stimulation.

EXAMPLE 22

LHL.seq INDUCED MHC CLASS II

LHL.seq was compared in its potential to ensure proper upregulation of MHC class II on stimulated B cells. Anti-IgM antibodies (20 μg/ml) as well as LHL. seq (1 μg/ml) blocked with huIgG (500 μg/ml) were included as controls. The method used was as described in Example 21.

Upregulation of MHC Class II molecules on B cells is a prerequisite to receive T cell help in vivo.

Overnight stimulation of C3H/HeJ lymph node cells with anti-IgM antibodies as well as LHL.seq did result in increased FSC and upregulation of MHC class II. LHL.seq's activities were completely blocked by addition of 500 μg/ml huIgG to the cultures.

EXAMPLE 23

LHL.seq INDUCED PROLIFERATION IN A DOSE DEPENDENT FASHION

Serial dilutions of LHL.seq were used to stimulate B cell proliferation. The experiment demonstrated that LHL.seq's biological properties are similar to conventional B cell mitogens like anti-IgM antibodies. Thus, dose-response curves for stimulation of either mesenteric lymphnode cells from C3H/HeJ and splenocytes from CBA/J were obtained.

EXAMPLE 24

TLHL INDUCED B CELL ACTIVATION

LHL.seq, TLHL and TEV-cleaved TLHL were tested for their ability to activate B cells as measured by the induction of cell surface expression of the activation markers B7-1 (CD86) and B7-2 (CD80) and by entry of B cells into cell cycle. Levels of expression of B7-1 and B7-2 were determined by flow cytometry (FACS) with fluorescence-labelled monoclonal antibodies while proliferation was monitored by an increase in cell size by Forward Light Scatter (FSC) and by $^3$H-thymidine-uptake assays.

The method employed as described in Example 21.

Overnight stimulation of C3H/HeJ lymph node cells with LPS did not result in B cell activation whereas stimulation with either anti-IgM antibodies or LHL.seq did as measured by an increased FSC and upregulation of B7-2. The characteristic potency of LHL.seq is demonstrated by the strong induction of B7-1 expression after overnight incubation. Anti-IgM induces B7-1 on day 2–3 of stimulation.

TLHL, however, activated B cells to the same extent as LHL.seq. This was unexpected since it was presumed that blocking one L domain with a covalently linked kappa would prevent crosslinking of immunoglobulin on the B cell surface. Prevention of crosslinking should result in no or significantly lower B cell activation than that achieved with equal amounts of LHL.seq. TEV-cleaved TLHL, which results in omp-kappa (see below) plus the LHL.seq part, gave much lower B cell activation than uncleaved TLHL as indicated by less B7-1 and B7-2 upregulation and lower FSC increase.

Splenocytes from CBA/J mice were centrifuged in Nycodenz (1.091 g/cm$^3$) to remove dead cells and rbc. This was followed by 1 hour adherence on plastic at 37° C. to remove adherent cells. Splenocytes were then stimulated in triplicate cultures at 2×10$^5$/well in flat bottom 96-well plates in complete RPMI+10% v/v FCS medium at 37° C. for 2 days. Cells were pulsed for the last 6 hours with $^3$H-thymidine. DNA was then harvested onto glassfibre filters and incorporation of $^3$H-thymidine was measured in a β-counter.

The results obtained by FACS analysis were confirmed by the proliferation data; TLHL and LHL.seq induced equivalent B cell proliferation while TEV-cleaved TLHL was about 70% less potent.

EXAMPLE 25

TEV-CLEAVED TLHL STIMULATION DATA CONFIRM OMP INDUCED MULTIMERISATION

The B cell activation data lead the inventors to the conclusion that both LHL, LHL.seq and TLHL exist in solution as multimeric molecules. While dimeric or oligomeric immunoglobulin-binding molecules such as anti-IgM antibodies induce B cell activation, multimers such as anti-IgD-dextran result in a significantly higher degree of B cell activation. This is also the case with LHL, LHL.seq and TLHL in the above experiments as demonstrated by the extensive upregulation of B7-1 after overnight culture. The multimerisation is facilitated by the ompA signal peptide (omp). It has been published by others that the ompA signal peptide forms multimers in aqueous solution. Evidence for LHL, LHL.seq and TLHL aggregation has also been obtained in HPLC studies.

A new recombinant LHL.seq protein lacking the ompA signal peptide, called LHL-omp, was engineered which also confirms these conclusions (see below).

EXAMPLE 26

TLHL MULTIMERISATION OVERCOMES "KAPPA-BLOCKING"

Although one 'L' domain should be blocked by kappa in TLHL, the multimerisation mediated by the omp allows several free 'L' domains to exist in one multimeric molecule $[TLHL]_n$. This will lead to extentive sIg crosslinking and full B cell activation as demonstrated.

EXAMPLE 27

GENERATION AND ANALYSIS OF LHL-OMP

LHL-omp was generated from LHL.seq via PCR with the proofreading polymerase Pfu eliminating the ompA signal sequence.

EXAMPLE 28

AFFINITY COLUMN PURIFICATION OF LHL-OMP

Although LHL-omp contains a Strep-tag, it could not be purified via the Streptavidin column using the standard protocol, indicating a lower avidity to the column matrix than that of LHL.seq. This lower avidity confirms the multimerisation of LHL.seq via omp, being the only difference between LHL.seq and LHL-omp. In agreement with this LHL-omp was readily purified over a huIgG affinity column.

EXAMPLE 29

LHL-OMP INDUCED B CELL ACTIVATION

The ability of LHL-omp to induce B cell activation was assessed by incubating splenocytes from C3H/HeJ mice for varying periods of time before analysing B7-1 and B7-2 expression levels on B cells as outlined above. The progression of B cells into cell cycle was monitored by FACS and proliferation assays.

Cells were prepared and cultured as described above. LPS (20 µg/ml) and anti-IgM (20 µg/ml) were used as controls.

Stimulation of C3H/HeJ splenocytes with LPS did not result in detectable B cell activation whereas treatment with either anti-IgM antibodies or LHL.seq induced B cell activation during overnight culture; increased FSC and B7-2 upregulation for anti-IgM antibodies and increased FSC and B7-1 and B7-2 expression for LHL.seq. LHL-omp, used at 2 µg/ml, was less potent than LHL.seq in inducing upregulation of B7-1, B7-2 and blasting of B cells, as indicated by the FSC profile. The unchanged FSC profile indicated that LHL-omp did not induce B cell proliferation. This was confirmed in proliferation assays.

B cells were stimulated simultaneously with LHL-omp and anti-CD40L antibodies (mAb FGK45.5 at a concentration of 0.5 µg/ml). Anti-CD40L antibodies served as a partial substitute for T cell help. The combination of sIg and helper T cell like signaling achieved good levels of B cell activation and proliferation. This could especially be demonstrated when using LHL-omp at a concentration of 125 ng/ml. 125 ng/ml induced no B cell activation on its own, however, when used in combination with the anti-CD40L antibody, which by itself is also of low potency, B7-1, B7-2 and FSC upregulation were achieved. Suggesting that LHL-omp and anti-CD40L antibodies can act synergistically.

EXAMPLE 30

UTILISING OMP TO DESIGN A NOVEL MULTIMERIC MITOGEN

Experimental data obtained show that the signal peptide from the outer membrane protein A (ompA) of *E. coli* induces aggregation of the recombinant proteins LHL.seq and TLHL. The ompA signal peptide (omp) is usually cleaved off once the protein reaches its destination, the bacterial periplasmic space. In the case of LHL, LHL.seq and TLHL, however, the secretion into the periplasm is impaired. All three proteins remain in the cytoplasm and the omp peptide forms their N-terminal part. The N-terminal omp peptide induces multimerisation as demonstrated by the potentiation of their biological activity as compared to the recombinant protein LHL-omp and TEV-cleaved TLHL.

The observation that omp induces multimerisation allows the design of simpler molecules with the same desired biological function as LHL, TLHL and CATAB. For this purpose we propose the following protein design. Above results demonstrate that the proteins described are not secreted into the periplasmic space. It should therefore be possible to produce proteins that have an omp peptide as their N-terminal part and L or HL as their C-terminal part. As omp allows the formation of multimers, this should result in the formation of $[ompL]_n$, hereafter called ompL, or $[ompHL]_n$ where n is equal or larger than 2.

EXAMPLE 31

MULTIMERISATION OF OMPL AND DESIGN OF FV-CATAB

Multimerisation of ompL generates a protein complex that should allow crosslinking of surface immunoglobulins in a similar fashion to LHL or LHL.seq. OmpL itself, however, is a relatively simple monomeric protein which needs only a single blocking entity. This blocking domain will be the below described scdsFv resulting the fusion protein ompL-linker-TEV-scdsFv (Fv-catAb). The reverse of this configuration, scdsFv-TEV-linker-Lomp (pFv-catAb) will also be generated, as this might allow for periplasmic secretion of pFv-catAb.The latter pFv-catAb requires the functional multimerisation and biological activity of Lomp, a protein with the reverse fusion order of ompL and the omp peptide at its C-terminal. All described recombinant proteins are tested in the experimental systems outlined above.

EXAMPLE 32

REDESIGN OF THE L DOMAIN BLOCKING ENTITY

Two potential problems are associated with the use of the LEN kappa light chain as a blocking domain for L. First, proteins (ie. LHL, LHL.seq and TLHL) are not secreted into the periplasmic space during expression in *E. coli*, which might cause folding problems in the kappa portion. Secondly, there are no direct means of purifying proteins with potentially correctly folded kappas in the described system, as antibodies against kappa would be bound by LHL.seq.

In order to allow for purification of correctly folded growth factor precursors, the blocking entity was therefore redesigned. Kappa will be replaced by a single chain (sc) antibody which is stabilised by an internal disulphide bridge (disulphide bridge stabilised, ds). This scdsFv will be derived from the extensively described plasmacytoma McPc603 [Freund et al. *Biochemistry* 33: 3296–3303, 1994] with anti-phosphorylcholine specificity. The phosphorylcholine-binding ability will facilitate the purification of correctly folded recombinant proteins via a phosphorylcholine affinity column.

EXAMPLE 33

POTENTIAL USE OF LHL/CATAB DERIVATIVES IN HUMANS

In order to enable production of catalytic antibodies in humans, slight modifications of the constructs need to be performed. The 'H' T cell epitope has to be exchanged for an "universal T cell epitope" which will be recognised by T cells in the majority of humans in conjunction with their more diverse MHC class II molecules.

EXAMPLE 34

GENERATION OF LgL

The periplasmic secretion of LHL (see PCT/AU97/00194, filed Mar. 26, 1997) fusion proteins like TLHL and others demonstrated that the H in LHL was quantitatively cleaved during transport. This made the purification of full-length products from the periplasmic space or the culture supernatant more difficult. In order to circumvent this proteolytic cleavage, the H-linker was replaced with a Glycine-Serine linker. This linker consists of a quadruple repeat of four glycine followed by one serine, (GGGGS)×4. In addition the proteins were fused to a hexa-his-Tag at their C-terminus to allow their purification over a nickel-chelate-column (FIG. 1).

EXAMPLE 35

STRUCTURE, ANALYSIS AND PURIFICATION OF LgL

From expression studies with ompL (OHL) the inventors demonstrated that the insertion of the H-linker sequence between ompA and L allowed secretion of L-proteins into the periplasm. In order to direct the expression of LgL into the periplasmic space, the ompA signal sequence as well as the H-linker sequence were therefore added to the N-terminus of the protein. This protein was named OHLgL (FIG. 1).

Figure 2:
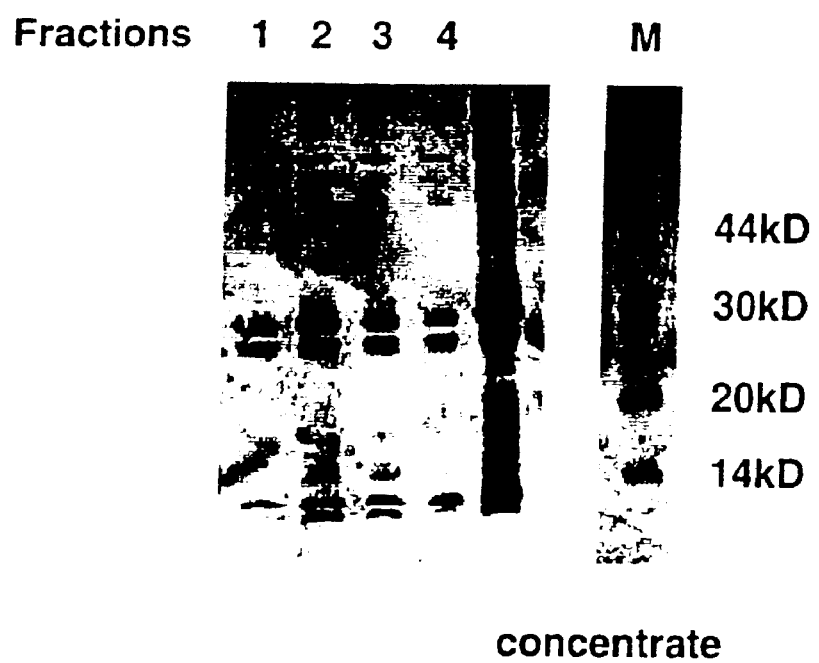
FIG. 2 is a photographic representation showing production of OHLgL in *E. coli* using 20% w/v PHAST-gels.
Figure 3:
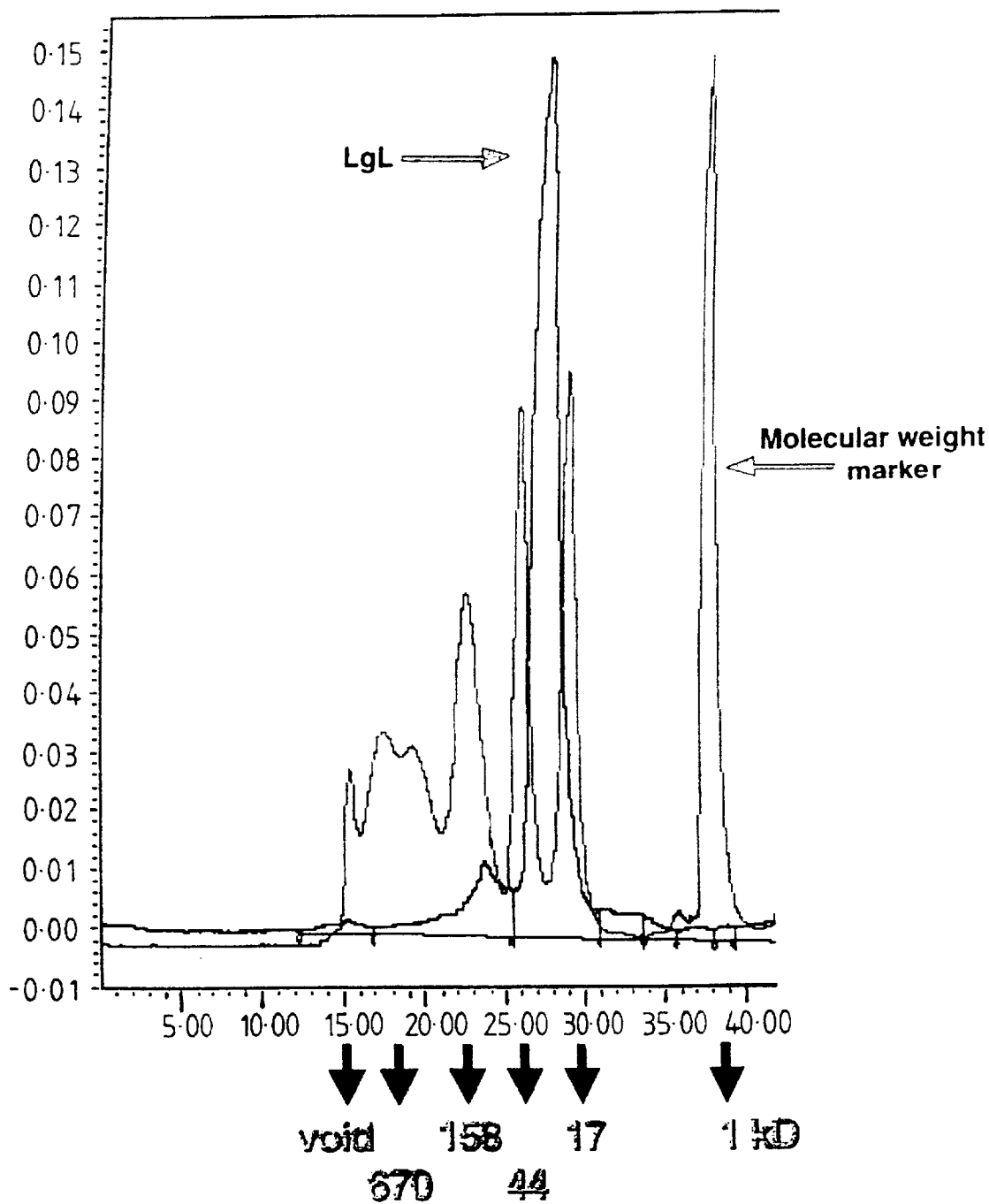
FIG. 3 is a graphical representation of the 280 nm absorbance trace showing purification of LgL on a HPLC superose 12 column.
Figure 4:
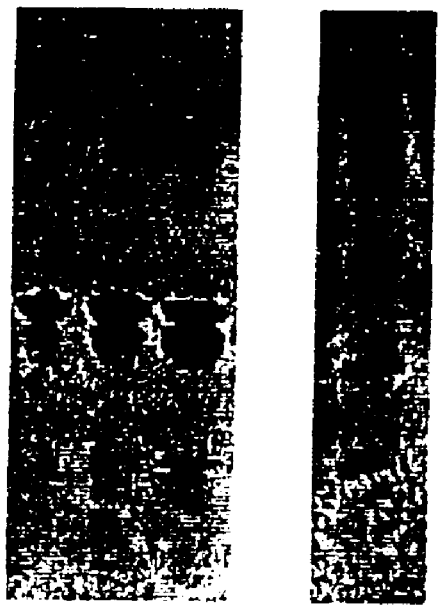
FIG. 4 is a photographic representation of LgL fractions from a HPLC superose 12 column on a 20% w/v PHAST gel.

OHLgL was expressed in *E. coli* strain DH10B by overnight induction with 400 μg/l anhydrotetracycline in non-buffered TB-media at room temperature. Cells were harvested and incubated in 500 mM sucrose, PBS on ice for 30 min. Cells were pelleted and LgL was purified from the supernatant containing the periplasmic proteins over a huIgG or a nickel-chelate column. LgL containing fractions (FIG. 2) as analysed on 20% w/v PHAST-gels were concentrated. LgL was further purified via a Superose 12 sizing column in PBS. The HPLC Superose12 sizing profile was used to determine the concentration of LgL in the final eluate according to the absorbance at 280 nm (FIG. 3). LgL containing fractions were again analysed on 20% w/v PHAST-gels and if necessary pooled for B cell activation assays (FIG. 4).

EXAMPLE 36

B CELL ACTIVATION POTENTIAL OF LgL

LgL was tested for its ability to activate B cells as compared to stimulation with anti-IgM and Lomp. Activation status was measured by the induction of cell surface expression of the activation markers B7-1 and B7-2 and by entry of B cells into cell cycle. Levels of expression of B7-1 and B7-2 were determined by flow cytometry (FACS) with fluorescence-labelled monoclonal antibodies while entry into cell cycle was monitored by an increase in cell size by Forward Light Scatter (FSC).

FACS were performed as follows. Mesenteric lymph node cells from C3H/HeJ mice were centrifuged in Nycodenz (1.091 g/cm$^3$) to remove dead cells and red blood cells (rbc). This was followed by 1 hour adherence on plastic at 37° C. to remove adherent cells such as macrophages. Lymph node cells were stimulated in triplicate cultures at 3×10$^5$/well in flat bottom 96-well plates in complete RPMI+10% v/v FCS medium at 37° C. overnight. Upregulation of activation markers on B cells was monitored by gating on B220$^+$ Thy$^-$ cells to identify B cells. Stimulation with LPS (20 μg/ml) and polyclonal F(ab)$_2$ anti-IgM antibodies (20 μg/ml) were included as controls. LgL was used at 1–10 μg/ml. C3H/HeJ mice were used as source of lymphocytes since this particular mouse strain is non-responsive to LPS. The use of this strain in combination with the LPS control effectively precludes the possibility that B cell stimulation induced by LgL is due to LPS (endotoxin) contamination of the bacterially expressed protein.

Figure 5:
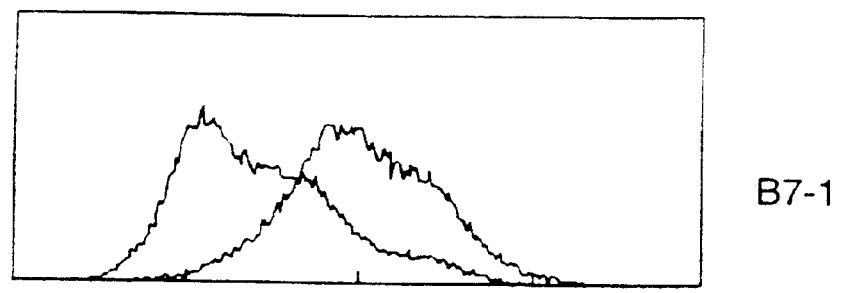
FIG. 5 is a graphical representation showing biological potency of LgL as demonstrated by B7-1 and B7-2 expression after overnight stimulation.
Figure 5:
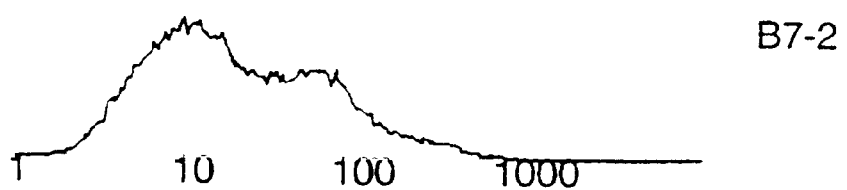

The results of the FACS analysis are as follows. Stimulation of C3H/HeJ lymph node cells with LPS did not result in B cell activation whereas stimulation with either anti-IgM antibodies or LgL did as measured by upregulation of B7-1 and B7-2. The characteristic potency of LgL is demonstrated by the strong induction of B7-1 expression already after overnight stimulation. Anti-IgM induces B7-1 on day 2–3 after stimulation (FIG. 5).

EXAMPLE 37

Figure 6:
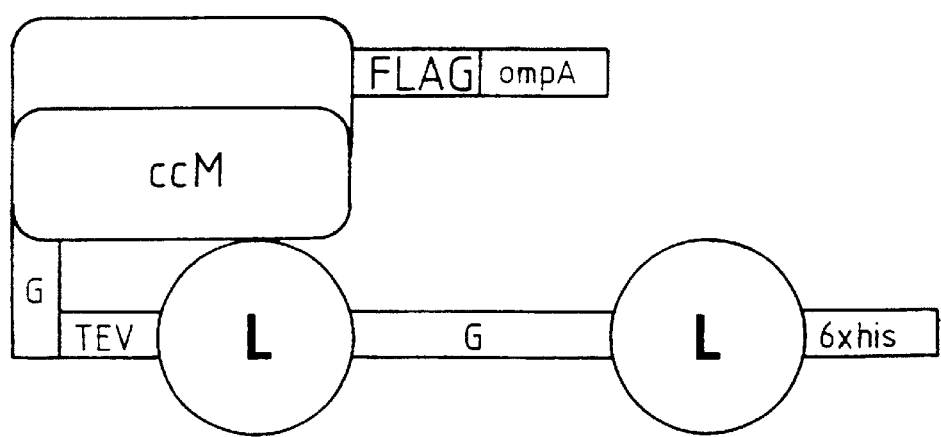
FIG. 6 is a diagrammatic representation showing structure of ccMTLgL comprising LgL with TEV cleavage signal and disulphide linked single chain Fv from McPc603.

GENERATION OF ccMTLgL ccMTLgL was generated by cloning the disulphide linked single chain Fv from McPc603 in place of the H sequence in OHLgL. ccM and LgL were separated by a glycine-serine linker and the TEV cleavage signal as used before in TLHL. A FLAG-tag was used between the ompA and ccM for purification purposes. The sequence of the individual protein domains was therefore as follows: O-FLAG-ccMTLgL-6xhis (FIG. 6). The nucleotide sequence and corresponding amino acid sequence for ccMTLgL is set forth in SEQ ID NOs: 15 and 16, respectively.

EXAMPLE 38

Figure 7:
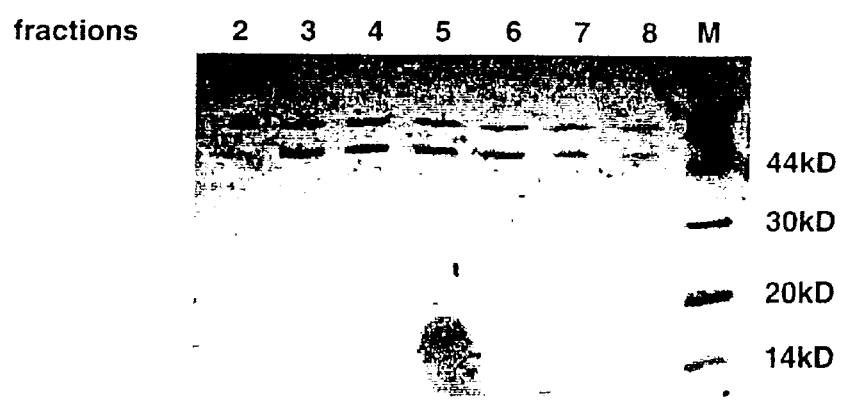
FIG. 7 is a photographic representation of ccMTLgL containing fractions from a FLAG M1 affinity column analysed on a PHAST-gel.
Figure 8:
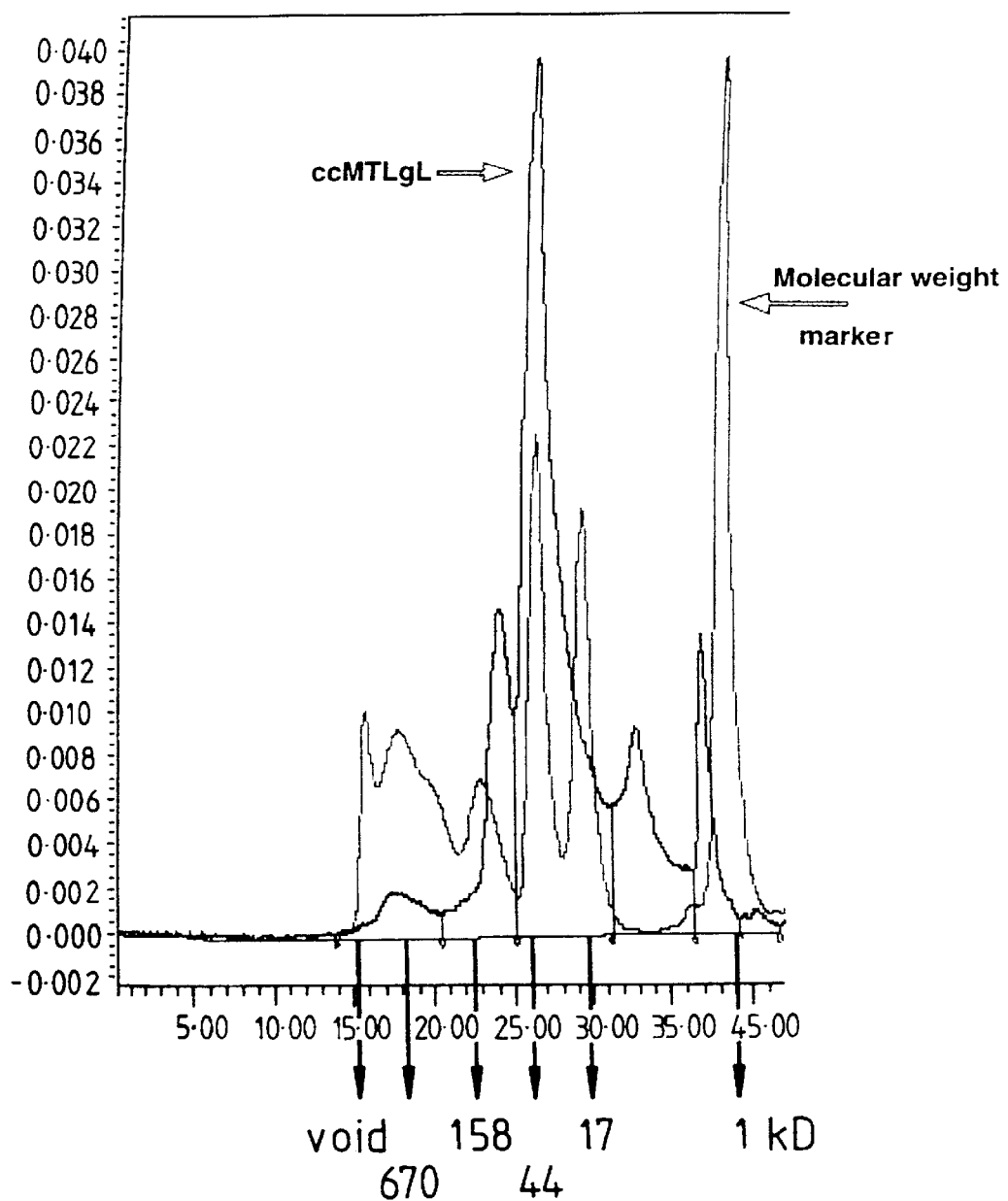
FIG. 8 is a graphical representation of the 280 nm absorbance trace of fractions containing ccMTLgL from an HPLC superose 12 gel.
Figure 9:
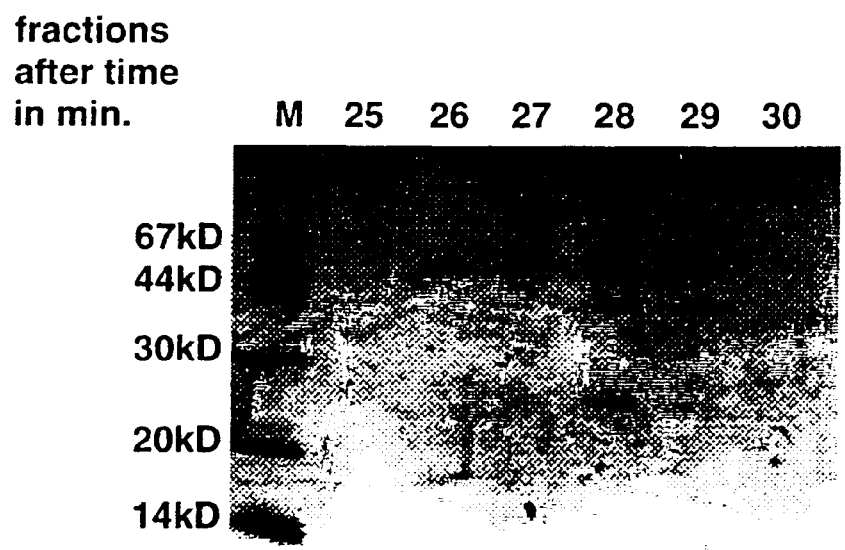
FIG. 9 is a photographic representation of ccMTLgL fractions from HPLC superose 12 gel analysed on PHAST gel.
Figure 10:
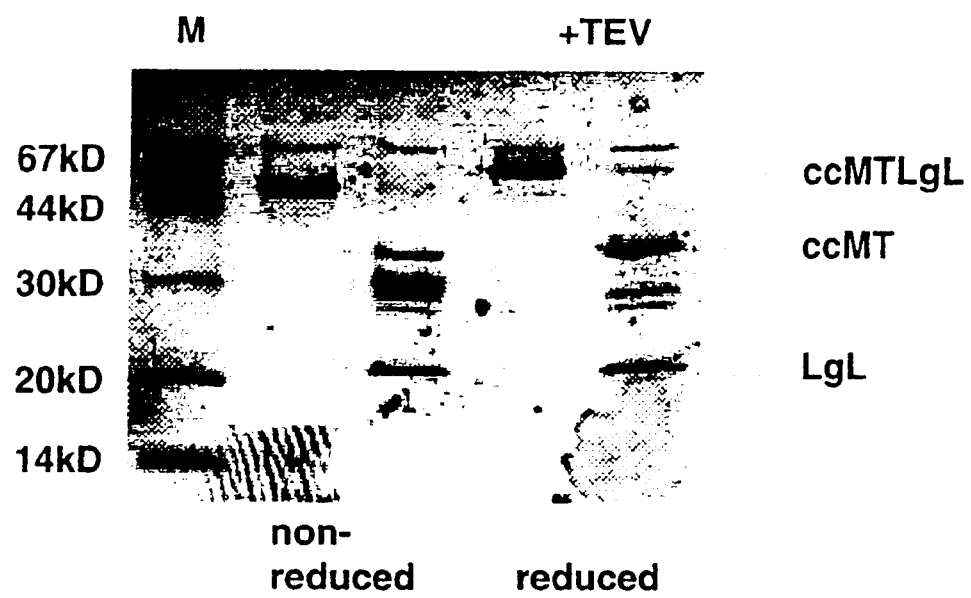
FIG. 10 is a photographic representation showing presence of inter-domain disulphide bond in ccMTLgL on 20% w/v PHAST gel under reducing and non-reducing conditions, before and after cleavage with TEV.
Figure 11:
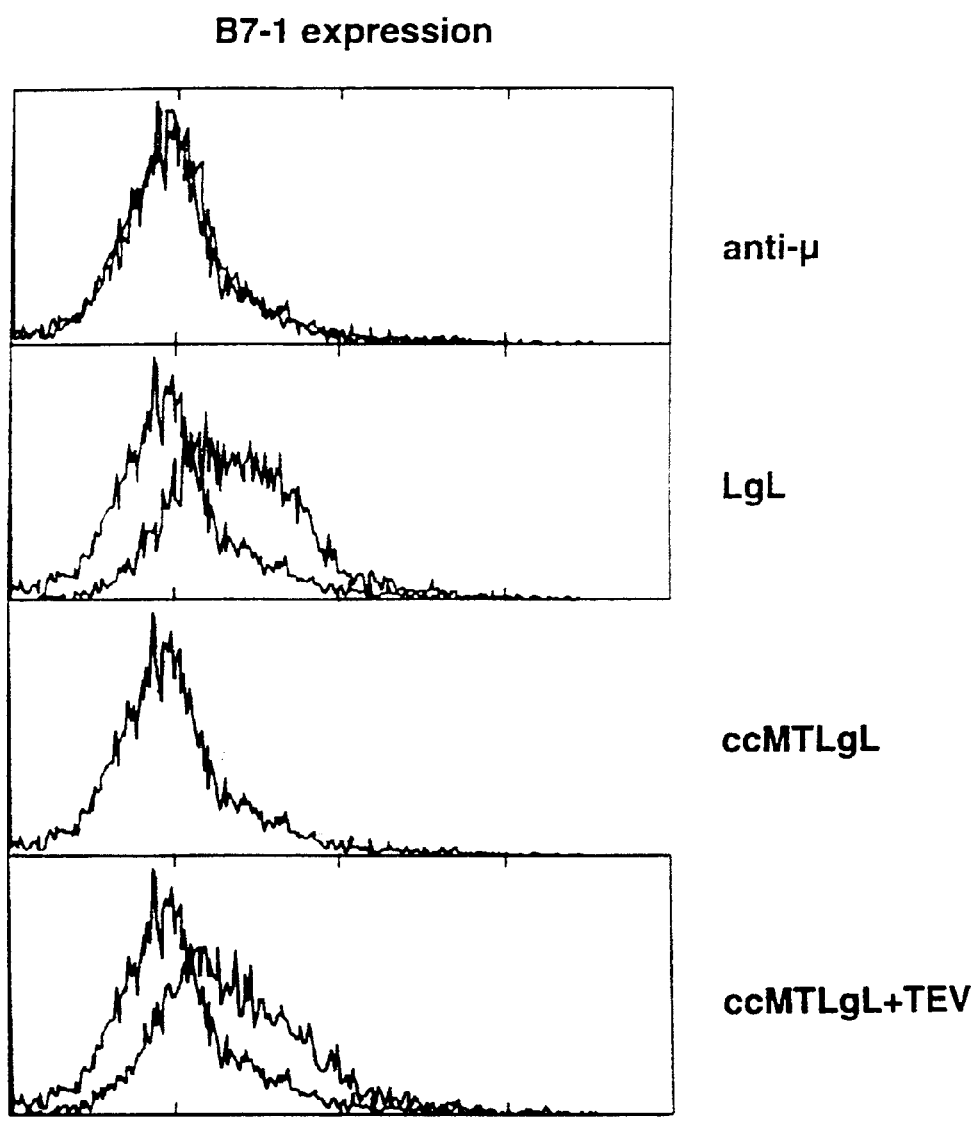
FIG. 11 is a graphical representation showing B7-1 expression after overnight stimulation of mesenteric lymph node cells with anti-$\mu$, LgL, ccMTLgL and ccMTLgL+TEV.
Figure 12:
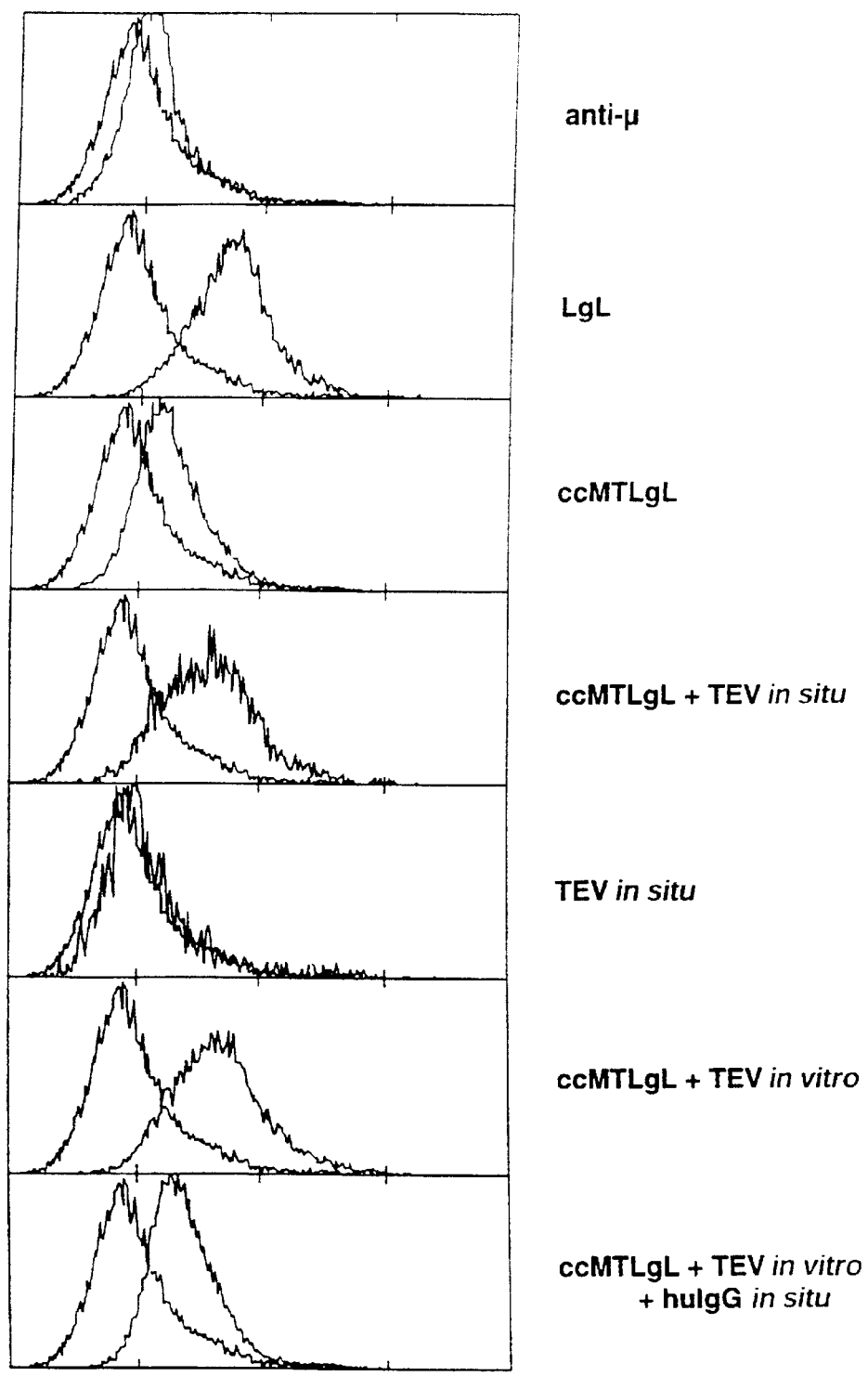
FIG. 12 is a graphical representation showing the results of repeating the experiment associated with FIG. 11 except that TEV is also added in situ to the overnight B cell cultures.
Figure 13:
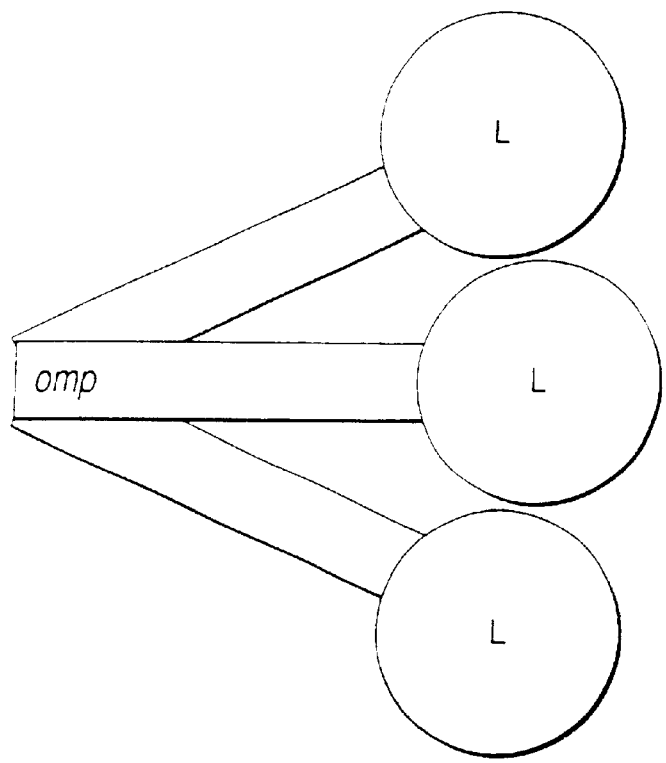
FIG. 13 is a schematic representation of ompL.
Figure 14:
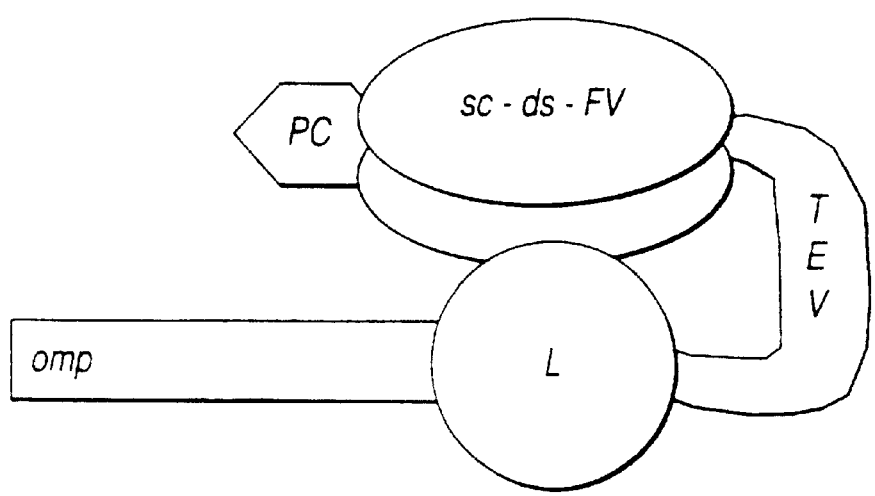
FIG. 14 is a schematic representation of Fv-catAb.
Figure 15:
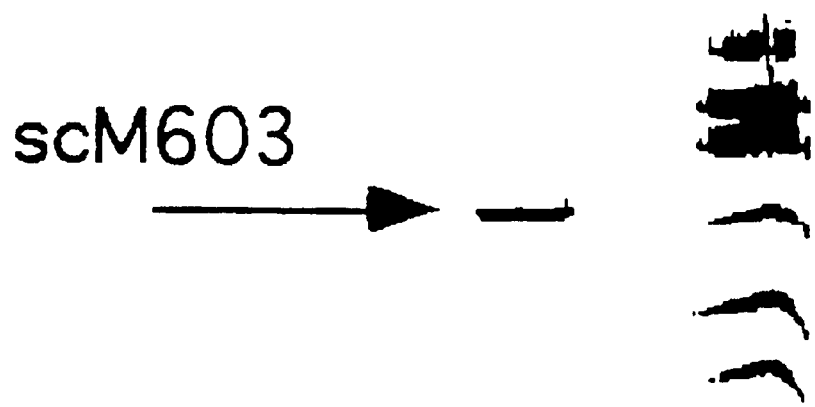
FIG. 15 is a photographic representation of a silver stained 20% w/v PAGE SDS PHAST-gel analysis of scM603 purified from periplasmic fraction via an L-column.

STRUCTURE, ANALYSIS AND PURIFICATION OF ccMTLgL ccMTLgL was expressed in *E. coli* strain DH10B by overnight induction with 400 μg anhydrotetracycline in non-buffered TB-media at room temperature. Cells were pelleted and ccMTLgL was purified from the concentrated supernatant over the Ca$^{++}$ dependent FLAG M1 affinity column. This FLAG M1 affinity column only purifies correctly processed free FLAG peptide at the N-terminus of a recombinant protein. ccMTLgL containing fractions (FIG. 7) as analysed on 20% w/v PHAST-gels were concentrated to <500 μl in 10.000 MW cut off spin concentrator. ccMTLgL was further purified via a Superose12 sizing column in PBS. The HPLC Superose12 sizing profile was used to determine the concentration of ccMTLgL in the final eluate according to the absorbance at 280 nm (FIG. 8). ccMTLgL containing fractions were again analysed on 20% w/v PHAST-gels and if necessary pooled for B cell activation assays (FIG. 9). The correct formation of the inter-domain disulphide bond was shown by running ccMTLgL on 20% w/v PHAST-gel under reducing and non-reducing condition before and after cleavage with TEV (FIG. 10).

EXAMPLE 39

TEV CATALYSIS INDUCED B CELL ACTIVATION BY ccMTLgL

25 μg of ccMTLgL in 140 μl of PBS were incubated with 50 Units TEV protease at 4° C. overnight. Complete cleavage into ccMT and LgL was verified on a 20% w/v PHAST-gel (FIG. 10).

Mesenteric LN cells (prepared as above) were stimulated overnight with controls (anti-IgM, LPS, LOMP, LgL and 2.5U TEV protease alone; all with and without huIgG) as well as 10 μg/ml ccMTLgL and 10 μg/ml ccMTLgL cleaved with TEV.

Results are shown in FIG. 11. ccMTLgL by itself gives no B cell stimulation whereas ccMTLgL cleaved with TEV shows B cell stimulation with upregulation of B7-1.

These results were reproduced three times. The same results were also obtained when 2.5U TEV protease were added in situ to the o/n B cell cultures (FIG. 12). Demonstrating that the in situ cleavage of ccMTLgL has the desired effect of liberating a B cell ritogen. This mimics the action of a catalytic antibody expressed by a B cell.

EXAMPLE 40

UTILISING OMP TO DESIGN A NOVEL MULTIMERIC MITOGEN ompL (FIG. 13) is secreted into the periplasmic space. The ompA signal peptide is, therefore, processed and cleaved off. ompL can be purified on a huIgG column. ompL fractions from huIgG column are concentrated over a Millipore concentrator and are further purified over a Superose-12 HPLC sizing column. ompL does not multimerise and, therefore, runs as a monomeric protein at approximately 10 kD.

Lomp is the reverse of ompL, carrying a modified ompA signal peptide at the C-terminus of LH. Lomp is expressed intracellularly and purified via huIgG and Superose-12 as described for ompL. ompL multimerises as predicted and elutes from the HPLC column in the void volume at >670 kD.

ompL and Lomp were tested for their ability to activate B cells. As measured by the induction of cell surface expression of activation markers and by entry into cell cycle. The method is as described above.

FACS analysis showed that this two day stimulation of lymph node cells with LPS did not result in B cell activation whereas stimulation with either anti-IgM antibodies or Lomp did as measured by an increased FSC and upregulation of B7-2. The characteristic potency of Lomp is demonstrated by the strong induction of B7-1 expression after incubation.

Lomp activity was blocked by the addition of 500 μg/ml soluble huIgG into the culture.

ompL has no activity in FACS or proliferation assays.

EXAMPLE 41

RE-DESIGN OF THE L DOMAIN BLOCKING ENTITY

A single chain Fv of McPc603 [scMcPc603] is expressed into the periplasmic space of *E. coli* DH10B. scMcPc603 can be purified on a L-column (FIG. 15). scMcPc603 is properly folded because it binds to the L domain. scMcPc603 can be utilised as a blocking entity for L in a catab construct. In one example, Fv-catAb is used (FIG. 14).

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

What is claimed is:

1. A growth factor precursor comprising a recombinant polypeptide chain or a molecule having modular peptide components or a synthetic equivalent thereof wherein said polypeptide chain or modular peptide molecule comprises at least one B cell surface molecule binding portion, at least one T cell surface molecule binding portion capable of providing T cell dependent help to a B cell, an antigen cleavable by a catalytic antibody and a peptide portion comprising domains from both a variable heavy chain and a variable light chain of an immunoglobulin and wherein said variable heavy chain and variable light chain domains in the growth factor precursor, associate together by intra- and/or inter-domain bonding and substantially prevent the at least one B cell surface molecule binding portion from interacting with a B cell surface molecule such that upon cleavage of said antigen by a catalytic antibody, the peptide comprising said variable heavy chain and variable light chain domain permits the at least one B cell surface molecule binding portion to interact with a B cell surface molecule.

2. A growth factor precursor comprising a recombinant polypeptide chain or a molecule having modular peptide components or a synthetic equivalent thereof wherein said polypeptide chain or modular peptide molecule comprises at least one B cell surface molecule binding portion, at least one T cell surface molecule binding portion capable of providing T cell dependent help to a B cell, an antigen cleavable by a catalytic antibody and a peptide portion comprising domains from both a variable heavy chain and a variable light chain of an immunoglobulin and wherein said variable heavy chain and variable light chain domains in the growth factor precursor associate together by intra- and/or inter-domain bonding and substantially prevent the at least one B cell surface molecule binding portion from interacting with a B cell surface molecule such that upon cleavage of said antigen by a catalytic antibody, the peptide comprising said variable heavy chain and variable light chain domain permits the at least one B cell surface molecule binding portion to interact with a B cell surface molecule wherein if said growth factor precursor comprises a single B cell surface molecule binding portion, then the growth factor precursor further comprises a multimerising inducing element.

3. A growth factor precursor according to claim 1 or 2 further comprising a multimerizing inducing element.

4. A growth factor precursor according to claim 1 or 2 further comprising a multimerizing inducing element wherein the multimerizing inducing element is a signal peptide.

5. A growth factor precursor according to claim 4 wherein the signal peptide is from ompA or a functional equivalent or derivative thereof.

6. A growth factor precursor according to claim 1 or 2 wherein the B cell surface molecule binding portion is the immunoglobulin binding domain from protein L from *Peptostreptococcus magnus* or a derivative or functional equivalent thereof.

7. A growth factor precursor according to claim 1 or 2 wherein said domains of said variable heavy chain and said variable light chain are stabilized by inter- and/or intra-domain disulphide bridges.

8. A recombinant or synthetic growth factor precursor comprising the structure:

$$I'AX_1[X_2]_d[X_3]_a[A]_rI''$$

wherein:

$X_1$ and $X_3$ are B cell surface molecule binding portions;

a is 0 or 1 or >1;

I' and I'' are either both present or only one is present and they may be the same or different and each is a blocking reagent for $X_1$ and/or $X_3$ and comprise domains from both a variable heavy chain and a variable light chain of an immunoglobulin, and wherein said variable heavy chain and variable light chain domains associate together by intra- and/or inter-domain bonding and substantially prevent at least one of $X_1$ or $X_3$ from interacting with a B cell surface molecule;

A is the target antigen for which a catalytic antibody is sought;

$X_2$ is an entity providing T cell dependent help to a B cell;

d is 0, 1 or >1;

r is 0, 1 or >1, wherein a catalytic antibody on the surface of said B cell is capable of cleaving all or part of A from said recombinant or synthetic molecule resulting in the molecule $[A']X_1X_2[X_3]_a[A']$ wherein A' is optionally present and is a portion of A after cleavage with the catalytic antibody wherein said resulting molecule is capable of interacting with said B cell surface molecule through at least one of $X_1$ or $X_3$ and inducing B cell mitogenesis of the B cell to which $X_1$ or $X_3$ bind.

9. A recombinant or synthetic growth factor precursor which comprises the structure:

$$[I'AX_1[X_2']_o[X_2X_3[A]_pI'']_n]_m$$

wherein:

I' and I'' are both present or only one is present and each is a blocking reagent for $X_1$ and/or $X_3$ and comprise domains from both a variable heavy chain and a variable light chain of an immunoglobulin, and wherein said variable heavy chain and variable light chain domains associate together by intra- and/or inter-domain bonding and substantially prevent at least one of $X_1$ or $X_3$ from interacting with a B cell surface molecule;

A is the target antigen for which a catalytic antibody is sought;

$X_1$ and $X_3$ are B cell surface molecule binding portions;

$X_2$ and $X_2'$ may be the same or different and each is an entity capable of providing T cell dependent help for a B cell;

o may be 0 or 1;

p may be 0 or 1;

n indicates the multimeric nature of the component in parentheses and may be 0, 1 or >1;

m indicates the multimeric nature of the component in parenthesis and may be 1 or >1.

* * * * *

```
                  SEQUENCE LISTING

<160> NUMBER OF SEQ ID NOS: 16

<210> SEQ ID NO 1
<211> LENGTH: 548
<212> TYPE: DNA
<213> ORGANISM: Artificial Sequence
<220> FEATURE:
<221> NAME/KEY: CDS
<222> LOCATION: (1)..(546)
<223> OTHER INFORMATION: Description of Artificial Sequence:LHL
      nucleotide sequence

<400> SEQUENCE: 1 atg aaa aag aca gct atc gcg att gca gtg gca ctg gct ggt ttc gct        48
Met Lys Lys Thr Ala Ile Ala Ile Ala Val Ala Leu Ala Gly Phe Ala
  1               5                  10                  15
```

| | | | | | | | | | | | | | | | |
|---|---|---|---|---|---|---|---|---|---|---|---|---|---|---|---|
| acc | gta | gcg | cag | gcc | gct | ccg | aaa | gat | aac | acg | gaa | gaa | gtc | acg | atc |
| Thr | Val | Ala | Gln | Ala | Ala | Pro | Lys | Asp | Asn | Thr | Glu | Glu | Val | Thr | Ile |
| | | | 20 | | | | | 25 | | | | | 30 | | |

96 aaa gcg aac ctg atc ttt gca aat ggt agc aca caa act gca gaa ttc    144
Lys Ala Asn Leu Ile Phe Ala Asn Gly Ser Thr Gln Thr Ala Glu Phe
         35                  40                  45 aaa ggt acc ttc gaa aaa gcg acc tcg gaa gct tat gcg tat gca gat    192
Lys Gly Thr Phe Glu Lys Ala Thr Ser Glu Ala Tyr Ala Tyr Ala Asp
 50                  55                  60 act ttg aag aaa gac aat ggt gaa tat act gta gat gtt gca gat aaa    240
Thr Leu Lys Lys Asp Asn Gly Glu Tyr Thr Val Asp Val Ala Asp Lys
 65                  70                  75                  80 ggt tac acc ctg aac atc aaa ttc gcg ggt aaa gaa gcg acc aac cgt    288
Gly Tyr Thr Leu Asn Ile Lys Phe Ala Gly Lys Glu Ala Thr Asn Arg
             85                  90                  95 aac acc gac ggt tcc acc gac tac ggt atc tta cag atc aac tct cgt    336
Asn Thr Asp Gly Ser Thr Asp Tyr Gly Ile Leu Gln Ile Asn Ser Arg
             100                 105                 110 tgg ggt ggt ctg acc ctg aaa gaa gaa gtc acg atc aaa gcg aac ctg    384
Trp Gly Gly Leu Thr Leu Lys Glu Glu Val Thr Ile Lys Ala Asn Leu
         115                 120                 125 atc ttt gca aat ggt agc aca caa act gca gaa ttc aaa ggt acc ttc    432
Ile Phe Ala Asn Gly Ser Thr Gln Thr Ala Glu Phe Lys Gly Thr Phe
 130                 135                 140 gaa aaa gcg acc tcg gaa gct tat gcg tat gca gat act ttg aag aaa    480
Glu Lys Ala Thr Ser Glu Ala Tyr Ala Tyr Ala Asp Thr Leu Lys Lys
145                 150                 155                 160 gac aat ggt gaa tat act gta gat gtt gca gat aaa ggt tac acc ctg    528
Asp Asn Gly Glu Tyr Thr Val Asp Val Ala Asp Lys Gly Tyr Thr Leu
             165                 170                 175 aac atc aaa ttc gcg ggt ta                                         548
Asn Ile Lys Phe Ala Gly
             180

<210> SEQ ID NO 2
<211> LENGTH: 182
<212> TYPE: PRT
<213> ORGANISM: Artificial Sequence
<220> FEATURE:
<223> OTHER INFORMATION: Description of Artificial Sequence:LHL protein
      sequence

<400> SEQUENCE: 2

Met Lys Lys Thr Ala Ile Ala Ile Ala Val Ala Leu Ala Gly Phe Ala
 1               5                  10                  15

Thr Val Ala Gln Ala Ala Pro Lys Asp Asn Thr Glu Glu Val Thr Ile
             20                  25                  30

Lys Ala Asn Leu Ile Phe Ala Asn Gly Ser Thr Gln Thr Ala Glu Phe
         35                  40                  45

Lys Gly Thr Phe Glu Lys Ala Thr Ser Glu Ala Tyr Ala Tyr Ala Asp
 50                  55                  60

Thr Leu Lys Lys Asp Asn Gly Glu Tyr Thr Val Asp Val Ala Asp Lys
 65                  70                  75                  80

Gly Tyr Thr Leu Asn Ile Lys Phe Ala Gly Lys Glu Ala Thr Asn Arg
             85                  90                  95

Asn Thr Asp Gly Ser Thr Asp Tyr Gly Ile Leu Gln Ile Asn Ser Arg
             100                 105                 110

Trp Gly Gly Leu Thr Leu Lys Glu Glu Val Thr Ile Lys Ala Asn Leu
         115                 120                 125

```
Ile Phe Ala Asn Gly Ser Thr Gln Thr Ala Glu Phe Lys Gly Thr Phe
        130                 135                 140

Glu Lys Ala Thr Ser Glu Ala Tyr Ala Tyr Ala Asp Thr Leu Lys Lys
145                 150                 155                 160

Asp Asn Gly Glu Tyr Thr Val Asp Val Ala Asp Lys Gly Tyr Thr Leu
                165                 170                 175

Asn Ile Lys Phe Ala Gly
            180

<210> SEQ ID NO 3
<211> LENGTH: 1490
<212> TYPE: DNA
<213> ORGANISM: Artificial Sequence
<220> FEATURE:
<221> NAME/KEY: CDS
<222> LOCATION: (1)..(1488)
<223> OTHER INFORMATION: Description of Artificial Sequence:CATAB-TEV
      nucleotide sequence

<400> SEQUENCE: 3 atg aaa aag aca gct atc gcg att gca gtg gca ctg gct ggt ttc gct      48
Met Lys Lys Thr Ala Ile Ala Ile Ala Val Ala Leu Ala Gly Phe Ala
 1               5                  10                  15 acc gta gcg cag gcc gac tac aag gac gat gac gac aag gat atc gtg     96
Thr Val Ala Gln Ala Asp Tyr Lys Asp Asp Asp Asp Lys Asp Ile Val
            20                  25                  30 atg acc cag tct cca gac tcc ctg gct gtg tct ctg ggc gag cgt gcc    144
Met Thr Gln Ser Pro Asp Ser Leu Ala Val Ser Leu Gly Glu Arg Ala
        35                  40                  45 acc atc aat tgc aag tcc agc cag agt gtt tta tac agc tcc aac agc    192
Thr Ile Asn Cys Lys Ser Ser Gln Ser Val Leu Tyr Ser Ser Asn Ser
    50                  55                  60 aag aac tac ctg gct tgg tac cag cag aaa cca ggt cag cct cct aag    240
Lys Asn Tyr Leu Ala Trp Tyr Gln Gln Lys Pro Gly Gln Pro Pro Lys
65                  70                  75                  80 ctg ctc att tac tgg gca tct acc cgt gaa tcc ggc gtt cct gac cgt    288
Leu Leu Ile Tyr Trp Ala Ser Thr Arg Glu Ser Gly Val Pro Asp Arg
                85                  90                  95 ttc agt ggt agc ggt tct ggt aca gat ttc act ctc acc atc agc agc    336
Phe Ser Gly Ser Gly Ser Gly Thr Asp Phe Thr Leu Thr Ile Ser Ser
            100                 105                 110 ctc cag gct gaa gat gtg gca gtt tat tac tgc cag cag tat tac agt    384
Leu Gln Ala Glu Asp Val Ala Val Tyr Tyr Cys Gln Gln Tyr Tyr Ser
        115                 120                 125 acc ccg tac tcc ttc ggt cag ggt acc aaa ctg gaa atc aaa cgc tcc    432
Thr Pro Tyr Ser Phe Gly Gln Gly Thr Lys Leu Glu Ile Lys Arg Ser
    130                 135                 140 ggt agc ggt ggc ggt ggt tct ggt ggt ggt ggg agc tct ggt ggt ggc    480
Gly Ser Gly Gly Gly Gly Ser Gly Gly Gly Gly Ser Ser Gly Gly Gly
145                 150                 155                 160 tct ggt ggt ggt agc gaa aac ctg tac ttc cag ggt ggt agc gcc gaa    528
Ser Gly Gly Gly Ser Glu Asn Leu Tyr Phe Gln Gly Gly Ser Ala Glu
                165                 170                 175 gaa gtc acg atc aaa gcg aac ctg atc ttt gca aat ggt agc aca caa    576
Glu Val Thr Ile Lys Ala Asn Leu Ile Phe Ala Asn Gly Ser Thr Gln
            180                 185                 190 act gca gaa ttc aaa ggt acc ttc gaa aaa gcg acc tcg gaa gct tat    624
Thr Ala Glu Phe Lys Gly Thr Phe Glu Lys Ala Thr Ser Glu Ala Tyr
        195                 200                 205
```

| | | | | | | | | | | | | | | |
|---|---|---|---|---|---|---|---|---|---|---|---|---|---|---|
| gcg | tat | gca | gat | act | ttg | aag | aaa | gac | aat | ggt | gaa | tat | act | gta gat | 672 |
| Ala | Tyr | Ala | Asp | Thr | Leu | Lys | Lys | Asp | Asn | Gly | Glu | Tyr | Thr | Val Asp |
| | 210 | | | | | 215 | | | | | 220 | | | |

```
gcg tat gca gat act ttg aag aaa gac aat ggt gaa tat act gta gat        672
Ala Tyr Ala Asp Thr Leu Lys Lys Asp Asn Gly Glu Tyr Thr Val Asp
    210                 215                 220 gtt gca gat aaa ggt tac acc ctg aac atc aaa ttc gcg ggt aaa gaa        720
Val Ala Asp Lys Gly Tyr Thr Leu Asn Ile Lys Phe Ala Gly Lys Glu
225                 230                 235                 240 gcg acc aac cgt aac acc gac ggt tcc acc gac tac ggt atc tta cag        768
Ala Thr Asn Arg Asn Thr Asp Gly Ser Thr Asp Tyr Gly Ile Leu Gln
                245                 250                 255 atc aac tct cgt tgg ggt ggt ctg acc agc gcc gaa gaa gtc acg atc        816
Ile Asn Ser Arg Trp Gly Gly Leu Thr Ser Ala Glu Glu Val Thr Ile
            260                 265                 270 aaa gcg aac ctg atc ttt gca aat ggt agc aca caa act gca gaa ttc        864
Lys Ala Asn Leu Ile Phe Ala Asn Gly Ser Thr Gln Thr Ala Glu Phe
        275                 280                 285 aaa ggt acc ttc gaa aaa gcg acc tcg gaa gct tat gcg tat gca gat        912
Lys Gly Thr Phe Glu Lys Ala Thr Ser Glu Ala Tyr Ala Tyr Ala Asp
290                 295                 300 act ttg aag aaa gac aat ggt gaa tat act gta gat gtt gca gat aaa        960
Thr Leu Lys Lys Asp Asn Gly Glu Tyr Thr Val Asp Val Ala Asp Lys
305                 310                 315                 320 ggt tac acc ctg aac atc aaa ttc gcg ggt aaa gaa agc ggt ggc ggt       1008
Gly Tyr Thr Leu Asn Ile Lys Phe Ala Gly Lys Glu Ser Gly Gly Gly
                325                 330                 335 ggt tct ggt ggt ggt ggg agc ggc gcc ggt ggt ggc tct ggt ggt ggt       1056
Gly Ser Gly Gly Gly Gly Ser Gly Ala Gly Gly Gly Ser Gly Gly Gly
            340                 345                 350 agc gaa aac ctg tac ttc cag ggt ggt ggc ggt ggc agc ggc ggt ggt       1104
Ser Glu Asn Leu Tyr Phe Gln Gly Gly Gly Gly Gly Ser Gly Gly Gly
        355                 360                 365 ggt gat atc gtg atg acc cag tct cca gac tcc ctg gct gtg tct ctg       1152
Gly Asp Ile Val Met Thr Gln Ser Pro Asp Ser Leu Ala Val Ser Leu
370                 375                 380 ggc gag cgt gcc acc atc aat tgc aag tcc agc cag agt gtt tta tac       1200
Gly Glu Arg Ala Thr Ile Asn Cys Lys Ser Ser Gln Ser Val Leu Tyr
385                 390                 395                 400 agc tcc aac agc aag aac tac ctg gct tgg tac cag cag aaa cca ggt       1248
Ser Ser Asn Ser Lys Asn Tyr Leu Ala Trp Tyr Gln Gln Lys Pro Gly
                405                 410                 415 cag cct cct aag ctg ctc att tac tgg gca tct acc cgt gaa tcc ggc       1296
Gln Pro Pro Lys Leu Leu Ile Tyr Trp Ala Ser Thr Arg Glu Ser Gly
            420                 425                 430 gtt cct gac cgt ttc agt ggt agc ggt tct ggt aca gat ttc act ctc       1344
Val Pro Asp Arg Phe Ser Gly Ser Gly Ser Gly Thr Asp Phe Thr Leu
        435                 440                 445 acc atc agc agc ctc cag gct gaa gat gtg gca gtt tat tac tgc cag       1392
Thr Ile Ser Ser Leu Gln Ala Glu Asp Val Ala Val Tyr Tyr Cys Gln
450                 455                 460 cag tat tac agt acc ccg tac tcc ttc ggt cag ggt acc aaa ctg gaa       1440
Gln Tyr Tyr Ser Thr Pro Tyr Ser Phe Gly Gln Gly Thr Lys Leu Glu
465                 470                 475                 480 atc aaa cgc agc ggt agc gct tgg cgt cac ccg cag ttc ggt ggt taa      1488
Ile Lys Arg Ser Gly Ser Ala Trp Arg His Pro Gln Phe Gly Gly
                485                 490                 495 ta                                                                    1490

<210> SEQ ID NO 4
<211> LENGTH: 495
<212> TYPE: PRT
<213> ORGANISM: Artificial Sequence
```

-continued

```
<220> FEATURE:
<223> OTHER INFORMATION: Description of Artificial Sequence:CATA B-TEV
      protein sequence

<400> SEQUENCE: 4

Met Lys Lys Thr Ala Ile Ala Ile Ala Val Ala Leu Ala Gly Phe Ala
  1               5                  10                  15

Thr Val Ala Gln Ala Asp Tyr Lys Asp Asp Asp Lys Asp Ile Val
             20                  25                  30

Met Thr Gln Ser Pro Asp Ser Leu Ala Val Ser Leu Gly Glu Arg Ala
             35                  40                  45

Thr Ile Asn Cys Lys Ser Ser Gln Ser Val Leu Tyr Ser Ser Asn Ser
         50                  55                  60

Lys Asn Tyr Leu Ala Trp Tyr Gln Gln Lys Pro Gly Gln Pro Pro Lys
 65                  70                  75                  80

Leu Leu Ile Tyr Trp Ala Ser Thr Arg Glu Ser Gly Val Pro Asp Arg
                 85                  90                  95

Phe Ser Gly Ser Gly Ser Gly Thr Asp Phe Thr Leu Thr Ile Ser Ser
            100                 105                 110

Leu Gln Ala Glu Asp Val Ala Val Tyr Tyr Cys Gln Gln Tyr Tyr Ser
            115                 120                 125

Thr Pro Tyr Ser Phe Gly Gln Gly Thr Lys Leu Glu Ile Lys Arg Ser
130                 135                 140

Gly Ser Gly Gly Gly Gly Ser Gly Gly Gly Gly Ser Gly Gly Gly Gly
145                 150                 155                 160

Ser Gly Gly Gly Ser Glu Asn Leu Tyr Phe Gln Gly Gly Ser Ala Glu
                165                 170                 175

Glu Val Thr Ile Lys Ala Asn Leu Ile Phe Ala Asn Gly Ser Thr Gln
            180                 185                 190

Thr Ala Glu Phe Lys Gly Thr Phe Glu Lys Ala Thr Ser Glu Ala Tyr
            195                 200                 205

Ala Tyr Ala Asp Thr Leu Lys Lys Asp Asn Gly Glu Tyr Thr Val Asp
        210                 215                 220

Val Ala Asp Lys Gly Tyr Thr Leu Asn Ile Lys Phe Ala Gly Lys Glu
225                 230                 235                 240

Ala Thr Asn Arg Asn Thr Asp Gly Ser Thr Asp Tyr Gly Ile Leu Gln
                245                 250                 255

Ile Asn Ser Arg Trp Gly Gly Leu Thr Ser Ala Glu Glu Val Thr Ile
            260                 265                 270

Lys Ala Asn Leu Ile Phe Ala Asn Gly Ser Thr Gln Thr Ala Glu Phe
        275                 280                 285

Lys Gly Thr Phe Glu Lys Ala Thr Ser Glu Ala Tyr Ala Tyr Ala Asp
    290                 295                 300

Thr Leu Lys Lys Asp Asn Gly Glu Tyr Thr Val Asp Val Ala Asp Lys
305                 310                 315                 320

Gly Tyr Thr Leu Asn Ile Lys Phe Ala Gly Lys Glu Ser Gly Gly Gly
                325                 330                 335

Gly Ser Gly Gly Gly Ser Gly Ala Gly Gly Ser Gly Gly Gly
            340                 345                 350

Ser Glu Asn Leu Tyr Phe Gln Gly Gly Gly Gly Ser Gly Gly Gly
        355                 360                 365

Gly Asp Ile Val Met Thr Gln Ser Pro Asp Ser Leu Ala Val Ser Leu
    370                 375                 380
```

```
Gly Glu Arg Ala Thr Ile Asn Cys Lys Ser Ser Gln Ser Val Leu Tyr
385                 390                 395                 400

Ser Ser Asn Ser Lys Asn Tyr Leu Ala Trp Tyr Gln Gln Lys Pro Gly
            405                 410                 415

Gln Pro Pro Lys Leu Leu Ile Tyr Trp Ala Ser Thr Arg Glu Ser Gly
        420                 425                 430

Val Pro Asp Arg Phe Ser Gly Ser Gly Ser Gly Thr Asp Phe Thr Leu
        435                 440                 445

Thr Ile Ser Ser Leu Gln Ala Glu Asp Val Ala Val Tyr Tyr Cys Gln
    450                 455                 460

Gln Tyr Tyr Ser Thr Pro Tyr Ser Phe Gly Gln Gly Thr Lys Leu Glu
465                 470                 475                 480

Ile Lys Arg Ser Gly Ser Ala Trp Arg His Pro Gln Phe Gly Gly
            485                 490                 495

<210> SEQ ID NO 5
<211> LENGTH: 1031
<212> TYPE: DNA
<213> ORGANISM: Artificial Sequence
<220> FEATURE:
<221> NAME/KEY: CDS
<222> LOCATION: (1)..(1029)
<223> OTHER INFORMATION: Description of Artificial Sequence:TLHL
      nucleotide sequence

<400> SEQUENCE: 5 atg aaa aag aca gct atc gcg att gca gtg gca ctg gct ggt ttc gct      48
Met Lys Lys Thr Ala Ile Ala Ile Ala Val Ala Leu Ala Gly Phe Ala
1               5                   10                  15 acc gta gcg cag gcc gac tac aag gac gat gac gac aag gat atc gtg     96
Thr Val Ala Gln Ala Asp Tyr Lys Asp Asp Asp Asp Lys Asp Ile Val
            20                  25                  30 atg acc cag tct cca gac tcc ctg gct gtg tct ctg ggc gag cgt gcc    144
Met Thr Gln Ser Pro Asp Ser Leu Ala Val Ser Leu Gly Glu Arg Ala
        35                  40                  45 acc atc aat tgc aag tcc agc cag agt gtt tta tac agc tcc aac agc    192
Thr Ile Asn Cys Lys Ser Ser Gln Ser Val Leu Tyr Ser Ser Asn Ser
    50                  55                  60 aag aac tac ctg gct tgg tac cag cag aaa cca ggt cag cct cct aag    240
Lys Asn Tyr Leu Ala Trp Tyr Gln Gln Lys Pro Gly Gln Pro Pro Lys
65                  70                  75                  80 ctg ctc att tac tgg gca tct acc cgt gaa tcc ggc gtt cct gac cgt    288
Leu Leu Ile Tyr Trp Ala Ser Thr Arg Glu Ser Gly Val Pro Asp Arg
                85                  90                  95 ttc agt ggt agc ggt tct ggt aca gat ttc act ctc acc atc agc agc    336
Phe Ser Gly Ser Gly Ser Gly Thr Asp Phe Thr Leu Thr Ile Ser Ser
            100                 105                 110 ctc cag gct gaa gat gtg gca gtt tat tac tgc cag cag tat tac agt    384
Leu Gln Ala Glu Asp Val Ala Val Tyr Tyr Cys Gln Gln Tyr Tyr Ser
        115                 120                 125 acc ccg tac tcc ttc ggt cag ggt acc aaa ctg gaa atc aaa cgc tcc    432
Thr Pro Tyr Ser Phe Gly Gln Gly Thr Lys Leu Glu Ile Lys Arg Ser
    130                 135                 140 ggt agc ggt ggc ggt ggt tct ggt ggt ggt ggg agc tct ggt ggt ggc    480
Gly Ser Gly Gly Gly Gly Ser Gly Gly Gly Gly Ser Ser Gly Gly Gly
145                 150                 155                 160 tct ggt ggt ggt agc gaa aac ctg tac ttc cag ggt ggt agc gcc gaa    528
Ser Gly Gly Gly Ser Glu Asn Leu Tyr Phe Gln Gly Gly Ser Ala Glu
                165                 170                 175
```

-continued

```
gaa gtc acg atc aaa gcg aac ctg atc ttt gca aat ggt agc aca caa       576
Glu Val Thr Ile Lys Ala Asn Leu Ile Phe Ala Asn Gly Ser Thr Gln
        180                 185                 190 act gca gaa ttc aaa ggt acc ttc gaa aaa gcg acc tcg gaa gct tat       624
Thr Ala Glu Phe Lys Gly Thr Phe Glu Lys Ala Thr Ser Glu Ala Tyr
            195                 200                 205 gcg tat gca gat act ttg aag aaa gac aat ggt gaa tat act gta gat       672
Ala Tyr Ala Asp Thr Leu Lys Lys Asp Asn Gly Glu Tyr Thr Val Asp
        210                 215                 220 gtt gca gat aaa ggt tac acc ctg aac atc aaa ttc gcg ggt aaa gaa       720
Val Ala Asp Lys Gly Tyr Thr Leu Asn Ile Lys Phe Ala Gly Lys Glu
225                 230                 235                 240 gcg acc aac cgt aac acc gac ggt tcc acc gac tac ggt atc tta cag       768
Ala Thr Asn Arg Asn Thr Asp Gly Ser Thr Asp Tyr Gly Ile Leu Gln
                245                 250                 255 atc aac tct cgt tgg ggt ggt ctg acc agc gcc gaa gaa gtc acg atc       816
Ile Asn Ser Arg Trp Gly Gly Leu Thr Ser Ala Glu Glu Val Thr Ile
            260                 265                 270 aaa gcg aac ctg atc ttt gca aat ggt agc aca caa act gca gaa ttc       864
Lys Ala Asn Leu Ile Phe Ala Asn Gly Ser Thr Gln Thr Ala Glu Phe
        275                 280                 285 aaa ggt acc ttc gaa aaa gcg acc tcg gaa gct tat gcg tat gca gat       912
Lys Gly Thr Phe Glu Lys Ala Thr Ser Glu Ala Tyr Ala Tyr Ala Asp
    290                 295                 300 act ttg aag aaa gac aat ggt gaa tat act gta gat gtt gca gat aaa       960
Thr Leu Lys Lys Asp Asn Gly Glu Tyr Thr Val Asp Val Ala Asp Lys
305                 310                 315                 320 ggt tac acc ctg aac atc aaa ttc gcg ggt aaa gaa agc gct tgg cgt      1008
Gly Tyr Thr Leu Asn Ile Lys Phe Ala Gly Lys Glu Ser Ala Trp Arg
                325                 330                 335 cac ccg cag ttc ggt ggt taa ta                                       1031
His Pro Gln Phe Gly Gly
            340
```

<210> SEQ ID NO 6
<211> LENGTH: 342
<212> TYPE: PRT
<213> ORGANISM: Artificial Sequence
<220> FEATURE:
<223> OTHER INFORMATION: Description of Artificial Sequence:TLHL protein sequence

<400> SEQUENCE: 6

```
Met Lys Lys Thr Ala Ile Ala Ile Ala Val Ala Leu Ala Gly Phe Ala
  1               5                  10                  15

Thr Val Ala Gln Ala Asp Tyr Lys Asp Asp Asp Lys Asp Ile Val
             20                  25                  30

Met Thr Gln Ser Pro Asp Ser Leu Ala Val Ser Leu Gly Glu Arg Ala
         35                  40                  45

Thr Ile Asn Cys Lys Ser Ser Gln Ser Val Leu Tyr Ser Ser Asn Ser
     50                  55                  60

Lys Asn Tyr Leu Ala Trp Tyr Gln Gln Lys Pro Gly Gln Pro Pro Lys
 65                  70                  75                  80

Leu Leu Ile Tyr Trp Ala Ser Thr Arg Glu Ser Gly Val Pro Asp Arg
                 85                  90                  95

Phe Ser Gly Ser Gly Ser Gly Thr Asp Phe Thr Leu Thr Ile Ser Ser
            100                 105                 110

Leu Gln Ala Glu Asp Val Ala Val Tyr Tyr Cys Gln Gln Tyr Tyr Ser
        115                 120                 125
```

```
Thr Pro Tyr Ser Phe Gly Gln Gly Thr Lys Leu Glu Ile Lys Arg Ser
    130                 135                 140

Gly Ser Gly Gly Gly Ser Gly Gly Gly Ser Ser Gly Gly
145                 150                 155                 160

Ser Gly Gly Gly Ser Glu Asn Leu Tyr Phe Gln Gly Gly Ser Ala Glu
                165                 170                 175

Glu Val Thr Ile Lys Ala Asn Leu Ile Phe Ala Asn Gly Ser Thr Gln
            180                 185                 190

Thr Ala Glu Phe Lys Gly Thr Phe Glu Lys Ala Thr Ser Glu Ala Tyr
        195                 200                 205

Ala Tyr Ala Asp Thr Leu Lys Lys Asp Asn Gly Glu Tyr Thr Val Asp
    210                 215                 220

Val Ala Asp Lys Gly Tyr Thr Leu Asn Ile Lys Phe Ala Gly Lys Glu
225                 230                 235                 240

Ala Thr Asn Arg Asn Thr Asp Gly Ser Thr Asp Tyr Gly Ile Leu Gln
                245                 250                 255

Ile Asn Ser Arg Trp Gly Gly Leu Thr Ser Ala Glu Val Thr Ile
            260                 265                 270

Lys Ala Asn Leu Ile Phe Ala Asn Gly Ser Thr Gln Thr Ala Glu Phe
        275                 280                 285

Lys Gly Thr Phe Glu Lys Ala Thr Ser Glu Ala Tyr Ala Tyr Ala Asp
    290                 295                 300

Thr Leu Lys Lys Asp Asn Gly Glu Tyr Thr Val Asp Val Ala Asp Lys
305                 310                 315                 320

Gly Tyr Thr Leu Asn Ile Lys Phe Ala Gly Lys Glu Ser Ala Trp Arg
                325                 330                 335

His Pro Gln Phe Gly Gly
            340
```

<210> SEQ ID NO 7
<211> LENGTH: 599
<212> TYPE: DNA
<213> ORGANISM: Artificial Sequence
<220> FEATURE:
<221> NAME/KEY: CDS
<222> LOCATION: (1)..(597)
<223> OTHER INFORMATION: Description of Artificial Sequence:LHL.seq
      nucleotide sequence

<400> SEQUENCE: 7

```
atg aaa aag aca gct atc gcg att gca gtg gca ctg gct ggt ttc gct      48
Met Lys Lys Thr Ala Ile Ala Ile Ala Val Ala Leu Ala Gly Phe Ala
  1               5                  10                  15 acc gta gcg cag gcc gac tac aag gac gat gac gac aag ggc gcc gaa      96
Thr Val Ala Gln Ala Asp Tyr Lys Asp Asp Asp Asp Lys Gly Ala Glu
             20                  25                  30 gaa gtc acg atc aaa gcg aac ctg atc ttt gca aat ggt agc aca caa     144
Glu Val Thr Ile Lys Ala Asn Leu Ile Phe Ala Asn Gly Ser Thr Gln
         35                  40                  45 act gca gaa ttc aaa ggt acc ttc gaa aaa gcg acc tcg gaa gct tat     192
Thr Ala Glu Phe Lys Gly Thr Phe Glu Lys Ala Thr Ser Glu Ala Tyr
     50                  55                  60 gcg tat gca gat act ttg aag aaa gac aat ggt gaa tat act gta gat     240
Ala Tyr Ala Asp Thr Leu Lys Lys Asp Asn Gly Glu Tyr Thr Val Asp
 65                  70                  75                  80 gtt gca gat aaa ggt tac acc ctg aac atc aaa ttc gcg ggt aaa gaa     288
Val Ala Asp Lys Gly Tyr Thr Leu Asn Ile Lys Phe Ala Gly Lys Glu
                 85                  90                  95
```

```
gcg acc aac cgt aac acc gac ggt tcc acc gac tac ggt atc tta cag       336
Ala Thr Asn Arg Asn Thr Asp Gly Ser Thr Asp Tyr Gly Ile Leu Gln
            100                 105                 110 atc aac tct cgt tgg ggt ggt ctg acc agc gcc gaa gaa gtc acg atc       384
Ile Asn Ser Arg Trp Gly Gly Leu Thr Ser Ala Glu Glu Val Thr Ile
        115                 120                 125 aaa gcg aac ctg atc ttt gca aat ggt agc aca caa act gca gaa ttc       432
Lys Ala Asn Leu Ile Phe Ala Asn Gly Ser Thr Gln Thr Ala Glu Phe
130                 135                 140 aaa ggt acc ttc gaa aaa gcg acc tcg gaa gct tat gcg tat gca gat       480
Lys Gly Thr Phe Glu Lys Ala Thr Ser Glu Ala Tyr Ala Tyr Ala Asp
145                 150                 155                 160 act ttg aag aaa gac aat ggt gaa tat act gta gat gtt gca gat aaa       528
Thr Leu Lys Lys Asp Asn Gly Glu Tyr Thr Val Asp Val Ala Asp Lys
                165                 170                 175 ggt tac acc ctg aac atc aaa ttc gcg ggt aaa gaa agc gct tgg cgt       576
Gly Tyr Thr Leu Asn Ile Lys Phe Ala Gly Lys Glu Ser Ala Trp Arg
            180                 185                 190 cac ccg cag ttc ggt ggt taa ta                                        599
His Pro Gln Phe Gly Gly
            195
```

<210> SEQ ID NO 8
<211> LENGTH: 198
<212> TYPE: PRT
<213> ORGANISM: Artificial Sequence
<220> FEATURE:
<223> OTHER INFORMATION: Description of Artificial Sequence:LHL.seq
      protein sequence

<400> SEQUENCE: 8

```
Met Lys Lys Thr Ala Ile Ala Ile Ala Val Ala Leu Ala Gly Phe Ala
 1               5                  10                  15

Thr Val Ala Gln Ala Asp Tyr Lys Asp Asp Asp Lys Gly Ala Glu
                20                  25                  30

Glu Val Thr Ile Lys Ala Asn Leu Ile Phe Ala Asn Gly Ser Thr Gln
            35                  40                  45

Thr Ala Glu Phe Lys Gly Thr Phe Glu Lys Ala Thr Ser Glu Ala Tyr
        50                  55                  60

Ala Tyr Ala Asp Thr Leu Lys Lys Asp Asn Gly Glu Tyr Thr Val Asp
65                  70                  75                  80

Val Ala Asp Lys Gly Tyr Thr Leu Asn Ile Lys Phe Ala Gly Lys Glu
                85                  90                  95

Ala Thr Asn Arg Asn Thr Asp Gly Ser Thr Asp Tyr Gly Ile Leu Gln
            100                 105                 110

Ile Asn Ser Arg Trp Gly Gly Leu Thr Ser Ala Glu Glu Val Thr Ile
        115                 120                 125

Lys Ala Asn Leu Ile Phe Ala Asn Gly Ser Thr Gln Thr Ala Glu Phe
    130                 135                 140

Lys Gly Thr Phe Glu Lys Ala Thr Ser Glu Ala Tyr Ala Tyr Ala Asp
145                 150                 155                 160

Thr Leu Lys Lys Asp Asn Gly Glu Tyr Thr Val Asp Val Ala Asp Lys
                165                 170                 175

Gly Tyr Thr Leu Asn Ile Lys Phe Ala Gly Lys Glu Ser Ala Trp Arg
            180                 185                 190

His Pro Gln Phe Gly Gly
            195
```

```
<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence:Flag epitope

<400> SEQUENCE: 9

Asp Tyr Lys Asp Asp Asp Asp Lys
 1               5

<210> SEQ ID NO 10
<211> LENGTH: 470
<212> TYPE: DNA
<213> ORGANISM: Artificial Sequence
<220> FEATURE:
<221> NAME/KEY: CDS
<222> LOCATION: (1)..(468)
<223> OTHER INFORMATION: Description of Artificial Sequence:Kappa
      nucleotide sequence

<400> SEQUENCE: 10 atg aaa aag aca gct atc gcg att gca gtg gca ctg gct ggt ttc gct      48
Met Lys Lys Thr Ala Ile Ala Ile Ala Val Ala Leu Ala Gly Phe Ala
 1               5                  10                  15 acc gta gcg cag gcc gac tac aag gac gat gac gac aag gat atc gtg      96
Thr Val Ala Gln Ala Asp Tyr Lys Asp Asp Asp Asp Lys Asp Ile Val
                20                  25                  30 atg acc cag tct cca gac tcc ctg gct gtg tct ctg ggc gag cgt gcc     144
Met Thr Gln Ser Pro Asp Ser Leu Ala Val Ser Leu Gly Glu Arg Ala
         35                  40                  45 acc atc aat tgc aag tcc agc cag agt gtt tta tac agc tcc aac agc     192
Thr Ile Asn Cys Lys Ser Ser Gln Ser Val Leu Tyr Ser Ser Asn Ser
     50                  55                  60 aag aac tac ctg gct tgg tac cag cag aaa cca ggt cag cct cct aag     240
Lys Asn Tyr Leu Ala Trp Tyr Gln Gln Lys Pro Gly Gln Pro Pro Lys
 65                  70                  75                  80 ctg ctc att tac tgg gca tct acc cgt gaa tcc ggc gtt cct gac cgt     288
Leu Leu Ile Tyr Trp Ala Ser Thr Arg Glu Ser Gly Val Pro Asp Arg
                 85                  90                  95 ttc agt ggt agc ggt tct ggt aca gat ttc act ctc acc atc agc agc     336
Phe Ser Gly Ser Gly Ser Gly Thr Asp Phe Thr Leu Thr Ile Ser Ser
            100                 105                 110 ctc cag gct gaa gat gtg gca gtt tat tac tgc cag cag tat tac agt     384
Leu Gln Ala Glu Asp Val Ala Val Tyr Tyr Cys Gln Gln Tyr Tyr Ser
        115                 120                 125 acc ccg tac tcc ttc ggt cag ggt acc aaa ctg gaa atc aaa cgc tcc     432
Thr Pro Tyr Ser Phe Gly Gln Gly Thr Lys Leu Glu Ile Lys Arg Ser
    130                 135                 140 ggt agc gct tgg cgt cac ccg cag ttc ggt ggt taa ta                  470
Gly Ser Ala Trp Arg His Pro Gln Phe Gly Gly
145                 150                 155

<210> SEQ ID NO 11
<211> LENGTH: 155
<212> TYPE: PRT
<213> ORGANISM: Artificial Sequence
<220> FEATURE:
<223> OTHER INFORMATION: Description of Artificial Sequence:Kappa
      protein sequence

<400> SEQUENCE: 11

Met Lys Lys Thr Ala Ile Ala Ile Ala Val Ala Leu Ala Gly Phe Ala
 1               5                  10                  15
```

```
Thr Val Ala Gln Ala Asp Tyr Lys Asp Asp Asp Lys Asp Ile Val
         20                  25                  30

Met Thr Gln Ser Pro Asp Ser Leu Ala Val Ser Leu Gly Glu Arg Ala
         35                  40                  45

Thr Ile Asn Cys Lys Ser Ser Gln Ser Val Leu Tyr Ser Ser Asn Ser
     50                  55                  60

Lys Asn Tyr Leu Ala Trp Tyr Gln Gln Lys Pro Gly Gln Pro Pro Lys
 65                  70                  75                  80

Leu Leu Ile Tyr Trp Ala Ser Thr Arg Glu Ser Gly Val Pro Asp Arg
                 85                  90                  95

Phe Ser Gly Ser Gly Ser Gly Thr Asp Phe Thr Leu Thr Ile Ser Ser
            100                 105                 110

Leu Gln Ala Glu Asp Val Ala Val Tyr Tyr Cys Gln Gln Tyr Tyr Ser
        115                 120                 125

Thr Pro Tyr Ser Phe Gly Gln Gly Thr Lys Leu Glu Ile Lys Arg Ser
    130                 135                 140

Gly Ser Ala Trp Arg His Pro Gln Phe Gly Gly
145                 150                 155
```

<210> SEQ ID NO 12
<211> LENGTH: 539
<212> TYPE: DNA
<213> ORGANISM: Artificial Sequence
<220> FEATURE:
<221> NAME/KEY: CDS
<222> LOCATION: (1)..(537)
<223> OTHER INFORMATION: Description of Artificial Sequence:LHL-omp
      nucleotide sequence

<400> SEQUENCE: 12

```
atg gac tac aag gac gat gac gac aag ggc gcc gaa gaa gtc acg atc      48
Met Asp Tyr Lys Asp Asp Asp Asp Lys Gly Ala Glu Glu Val Thr Ile
  1               5                  10                  15 aaa gcg aac ctg atc ttt gca aat ggt agc aca caa act gca gaa ttc      96
Lys Ala Asn Leu Ile Phe Ala Asn Gly Ser Thr Gln Thr Ala Glu Phe
             20                  25                  30 aaa ggt acc ttc gaa aaa gcg acc tcg gaa gct tat gcg tat gca gat     144
Lys Gly Thr Phe Glu Lys Ala Thr Ser Glu Ala Tyr Ala Tyr Ala Asp
         35                  40                  45 act ttg aag aaa gac aat ggt gaa tat act gta gat gtt gca gat aaa     192
Thr Leu Lys Lys Asp Asn Gly Glu Tyr Thr Val Asp Val Ala Asp Lys
     50                  55                  60 ggt tac acc ctg aac atc aaa ttc gcg ggt aaa gaa gcg acc aac cgt     240
Gly Tyr Thr Leu Asn Ile Lys Phe Ala Gly Lys Glu Ala Thr Asn Arg
 65                  70                  75                  80 aac acc gac ggt tcc acc gac tac ggt atc tta cag atc aac tct cgt     288
Asn Thr Asp Gly Ser Thr Asp Tyr Gly Ile Leu Gln Ile Asn Ser Arg
                 85                  90                  95 tgg ggt ggt ctg acc agc gcc gaa gaa gtc acg atc aaa gcg aac ctg     336
Trp Gly Gly Leu Thr Ser Ala Glu Glu Val Thr Ile Lys Ala Asn Leu
            100                 105                 110 atc ttt gca aat ggt agc aca caa act gca gaa ttc aaa ggt acc ttc     384
Ile Phe Ala Asn Gly Ser Thr Gln Thr Ala Glu Phe Lys Gly Thr Phe
        115                 120                 125 gaa aaa gcg acc tcg gaa gct tat gcg tat gca gat act ttg aag aaa     432
Glu Lys Ala Thr Ser Glu Ala Tyr Ala Tyr Ala Asp Thr Leu Lys Lys
    130                 135                 140 gac aat ggt gaa tat act gta gat gtt gca gat aaa ggt tac acc ctg     480
Asp Asn Gly Glu Tyr Thr Val Asp Val Ala Asp Lys Gly Tyr Thr Leu
145                 150                 155                 160
```

```
aac atc aaa ttc gcg ggt aaa gaa agc gct tgg cgt cac ccg cag ttc    528
Asn Ile Lys Phe Ala Gly Lys Glu Ser Ala Trp Arg His Pro Gln Phe
            165                 170                 175 ggt ggt taa ta                                                     539
Gly Gly
```

<210> SEQ ID NO 13
<211> LENGTH: 178
<212> TYPE: PRT
<213> ORGANISM: Artificial Sequence
<220> FEATURE:
<223> OTHER INFORMATION: Description of Artificial Sequence:LHL-omp
      protein sequence

<400> SEQUENCE: 13

```
Met Asp Tyr Lys Asp Asp Asp Lys Gly Ala Glu Glu Val Thr Ile
 1               5                  10                  15

Lys Ala Asn Leu Ile Phe Ala Asn Gly Ser Thr Gln Thr Ala Glu Phe
                 20                  25                  30

Lys Gly Thr Phe Glu Lys Ala Thr Ser Glu Ala Tyr Ala Tyr Ala Asp
             35                  40                  45

Thr Leu Lys Lys Asp Asn Gly Glu Tyr Thr Val Asp Val Ala Asp Lys
     50                  55                  60

Gly Tyr Thr Leu Asn Ile Lys Phe Ala Gly Lys Glu Ala Thr Asn Arg
 65                  70                  75                  80

Asn Thr Asp Gly Ser Thr Asp Tyr Gly Ile Leu Gln Ile Asn Ser Arg
                 85                  90                  95

Trp Gly Gly Leu Thr Ser Ala Glu Glu Val Thr Ile Lys Ala Asn Leu
                100                 105                 110

Ile Phe Ala Asn Gly Ser Thr Gln Thr Ala Glu Phe Lys Gly Thr Phe
            115                 120                 125

Glu Lys Ala Thr Ser Glu Ala Tyr Ala Tyr Ala Asp Thr Leu Lys Lys
        130                 135                 140

Asp Asn Gly Glu Tyr Thr Val Asp Val Ala Asp Lys Gly Tyr Thr Leu
145                 150                 155                 160

Asn Ile Lys Phe Ala Gly Lys Glu Ser Ala Trp Arg His Pro Gln Phe
                165                 170                 175

Gly Gly
```

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence:Strep-tag

<400> SEQUENCE: 14

```
Ala Trp Arg His Pro Gln Phe Gly Gly
 1               5
```

<210> SEQ ID NO 15
<211> LENGTH: 1479
<212> TYPE: DNA
<213> ORGANISM: Artificial Sequence
<220> FEATURE:
<223> OTHER INFORMATION: Description of Artificial Sequence:ccMTLgL
      nucleotide sequence

<400> SEQUENCE: 15

```
caaaaatcta gataacgagg gcaaaaaatg aaaaagacag ctatcgcgat tgcagtggca    60
```

```
ctggctggtt tcgctaccgt agcgcaggcc gactacaagg acgatgacga caagagcgag      120
gtgaagctgg tggaatctgg aggaggcttg gtacagcctg ggggttctct gagactctcc      180
tgtgcaactt ctgggttcac cttcagtgat ttctacatgg agtgggtccg ccagcctcca      240
gggaagagac tggagtggat tgctgcaagt agaaacaaag gtaataaata caacagaa        300 tacagtgcat ctgtgaaggg tcggttcatc gtctccagag acacttccca aagcatcctc      360
taccttcaga tgaatgccct gagagctgag gacacagcca tttattactg tgcaagaaat      420
tactacggta gtacctggtg cttcgatgtc tggggcgcag ggaccacggt caccgtctcc      480
tcaggtggtg gcggtggtag cggtggcggt ggttctggtg gtggtggtag cggtggtggt      540
ggttccgaca ttgtgatgac acagtctcca tcctccctga gtgtgtcagc aggagagaga      600
gtcactatga gttgcaagtc cagtcagagt ctgttaaaca gtggaaatca aagaacttc       660 ttggcctggt accagcagaa accagggcag cctcctaaac tgttgatctg cggggcatcc      720
actagggaat ctggggtccc tgatcgcttc acaggcagtg gatctggaac cgatttcact      780
cttaccatca gcagtgtgca ggctgaagac ctggcagttt attactgtca gaatgatcat      840
agttatccgc tcacgttcgg tgctgggacc aagctggagc tgaaacgtgc tagcggtggc      900
ggtggttctg gtggtggtgg agcggcgcc ggtggtggct ctggtggtgg tagcgaaaac      960
ctgtacttcc agggtggtgg cggtggcagc gctgaagaag tcacgatcaa agcgaacctg      1020
atctttgcaa atggtagcac acaaactgca gaattcaaag gtaccttcga aaaagcgacc      1080
tcggaagctt atgcgtatgc agatactttg aagaaagaca atggtgaata tactgtagat      1140
gttgcagata aaggttacac cctgaacatc aaattcgcgg gtaaagaagc tagcggtggc      1200
ggtggttctg gtggtggtgg ttctggtggc ggtggttctg gtggtggtgg ttctgctgaa      1260
gaagtcacga tcaaagcgaa cctgatcttt gcaaatggta gcacacaaac tgcagaattc      1320
aaaggtacct cgaaaaagc gacctcggaa gcttatgcgt atgcagatac tttgaagaaa      1380
gacaatggtg aatatactgt agatgttgca gataaaggtt acaccctgaa catcaaattc      1440
gcgggtaaag aagctcatca ccatcaccat cactaataa                             1479
```

<210> SEQ ID NO 16
<211> LENGTH: 482
<212> TYPE: PRT
<213> ORGANISM: Artificial Sequence
<220> FEATURE:
<223> OTHER INFORMATION: Description of Artificial Sequence:ccMTLgL
    protein sequence

<400> SEQUENCE: 16

Met Lys Lys Thr Ala Ile Ala Ile Ala Val Ala Leu Ala Gly Phe Ala
 1               5                  10                  15

Thr Val Ala Gln Ala Asp Tyr Lys Asp Asp Asp Lys Ser Glu Val
            20                  25                  30

Lys Leu Val Glu Ser Gly Gly Gly Leu Val Gln Pro Gly Gly Ser Leu
        35                  40                  45

Arg Leu Ser Cys Ala Thr Ser Gly Phe Thr Phe Ser Asp Phe Tyr Met
    50                  55                  60

Glu Trp Val Arg Gln Pro Pro Gly Lys Arg Leu Glu Trp Ile Ala Ala
65                  70                  75                  80

Ser Arg Asn Lys Gly Asn Lys Tyr Thr Thr Glu Tyr Ser Ala Ser Val
                85                  90                  95

Lys Gly Arg Phe Ile Val Ser Arg Asp Thr Ser Gln Ser Ile Leu Tyr
            100                 105                 110

```
Leu Gln Met Asn Ala Leu Arg Ala Glu Asp Thr Ala Ile Tyr Tyr Cys
        115                 120                 125

Ala Arg Asn Tyr Tyr Gly Ser Thr Trp Cys Phe Asp Val Trp Gly Ala
    130                 135                 140

Gly Thr Thr Val Thr Val Ser Ser Gly Gly Gly Gly Ser Gly Gly
145             150                 155                 160

Gly Gly Ser Gly Gly Gly Gly Ser Gly Gly Gly Ser Asp Ile Val
            165                 170                 175

Met Thr Gln Ser Pro Ser Ser Leu Ser Val Ser Ala Gly Glu Arg Val
        180                 185                 190

Thr Met Ser Cys Lys Ser Ser Gln Ser Leu Leu Asn Ser Gly Asn Gln
        195                 200                 205

Lys Asn Phe Leu Ala Trp Tyr Gln Gln Lys Pro Gly Gln Pro Pro Lys
        210                 215                 220

Leu Leu Ile Cys Gly Ala Ser Thr Arg Glu Ser Gly Val Pro Asp Arg
225                 230                 235                 240

Phe Thr Gly Ser Gly Ser Gly Thr Asp Phe Thr Leu Thr Ile Ser Ser
                245                 250                 255

Val Gln Ala Glu Asp Leu Ala Val Tyr Tyr Cys Gln Asn Asp His Ser
        260                 265                 270

Tyr Pro Leu Thr Phe Gly Ala Gly Thr Lys Leu Glu Leu Lys Arg Ala
        275                 280                 285

Ser Gly Gly Gly Gly Ser Gly Gly Gly Ser Gly Ala Gly Gly Gly
    290                 295                 300

Ser Gly Gly Gly Ser Glu Asn Leu Tyr Phe Gln Gly Gly Gly Gly Gly
305                 310                 315                 320

Ser Ala Glu Glu Val Thr Ile Lys Ala Asn Leu Ile Phe Ala Asn Gly
                325                 330                 335

Ser Thr Gln Thr Ala Glu Phe Lys Gly Thr Phe Glu Lys Ala Thr Ser
        340                 345                 350

Glu Ala Tyr Ala Tyr Ala Asp Thr Leu Lys Lys Asp Asn Gly Glu Tyr
        355                 360                 365

Thr Val Asp Val Ala Asp Lys Gly Tyr Thr Leu Asn Ile Lys Phe Ala
    370                 375                 380

Gly Lys Glu Ala Ser Gly Gly Gly Ser Gly Gly Gly Gly Ser Gly
385                 390                 395                 400

Gly Gly Ser Gly Gly Gly Gly Ser Ala Glu Glu Val Thr Ile Lys
            405                 410                 415

Ala Asn Leu Ile Phe Ala Asn Gly Ser Thr Gln Thr Ala Glu Phe Lys
        420                 425                 430

Gly Thr Phe Glu Lys Ala Thr Ser Glu Ala Tyr Ala Tyr Ala Asp Thr
        435                 440                 445

Leu Lys Lys Asp Asn Gly Glu Tyr Thr Val Asp Val Ala Asp Lys Gly
        450                 455                 460

Tyr Thr Leu Asn Ile Lys Phe Ala Gly Lys Glu Ala His His His
465                 470                 475                 480

His His
```